(12) United States Patent
Kondo et al.

(10) Patent No.: US 9,611,464 B2
(45) Date of Patent: Apr. 4, 2017

(54) THERMOSTABLE β-XYLOSIDASE BELONGING TO GH FAMILY 3

(71) Applicant: HONDA MOTOR CO., LTD., Minato-ku, Tokyo (JP)

(72) Inventors: Yasuhiro Kondo, Wako (JP); Yoshitsugu Hirose, Wako (JP); Asuka Yamaguchi, Wako (JP); Migiwa Suda, Wako (JP); Jiro Okuma, Wako (JP); Tomohiko Kato, Kisarazu (JP); Daisuke Shibata, Kisarazu (JP)

(73) Assignee: Honda Motor Co. Ltd., Tokyo (JP)

( * ) Notice: Subject to any disclaimer, the term of this patent is extended or adjusted under 35 U.S.C. 154(b) by 0 days.

(21) Appl. No.: 14/813,894

(22) Filed: Jul. 30, 2015

(65) Prior Publication Data
US 2016/0032265 A1 Feb. 4, 2016

(30) Foreign Application Priority Data
Aug. 4, 2014 (JP) ................. 2014-158650

(51) Int. Cl.
C12N 9/42 (2006.01)
C12P 21/04 (2006.01)
C12N 1/20 (2006.01)
C12N 15/00 (2006.01)
C07H 21/04 (2006.01)
A61K 38/00 (2006.01)
C12N 9/24 (2006.01)

(52) U.S. Cl.
CPC ........... *C12N 9/248* (2013.01); *C12N 9/2445* (2013.01); *C12Y 302/01037* (2013.01); *C07K 2319/00* (2013.01); *C07K 2319/02* (2013.01)

(58) Field of Classification Search
CPC .................................................. C12N 9/2445
See application file for complete search history.

(56) References Cited

U.S. PATENT DOCUMENTS 7,923,234 B2 * 4/2011 Thompson ..... C12Y 302/01037
435/200
2013/0330784 A1 12/2013 Reisinger et al.

FOREIGN PATENT DOCUMENTS

| DE | 102010042910 A1 | 4/2012 |
| JP | H11-507837 A | 7/1999 |
| JP | 11-313683 A | 11/1999 |
| JP | 2011-523346 A | 8/2011 |
| JP | 2013-059272 A | 4/2013 |
| WO | 97/00964 A1 | 1/1997 |
| WO | 2009/094187 A1 | 7/2009 |

OTHER PUBLICATIONS

Branden et al. Introduction to Protein Structure, Garland Publishing Inc., New York, p. 247, 1991.*
Search Report corresponding with Patent Application No. EP 15 17 8856 dated Dec. 7, 2015.
Manelius et al., "Some Properties of a Thermostable Beta-Xylosidase from Rhodothermus marinus," Applied Biochemistry and Biotechnology, 1994, pp. 39-48, vol. 44, Humana Press Inc.
Shag et al., "Purification and Characterization of a Thermostable Beta-Xylosidase from Thermoanaerobacter ethanolicus," Journal of Bacteriology, Sep. 1992, pp. 5848-5853, vol. 174, No. 18, American Society for Microbiology.
Kormelink et al., "Purification and characterization of three endo-(1,4)- Beta-xylanases and one Beta-xylosidase from Aspergillus awamori", Journal of Biotechnology, Feb. 1993, vol. 27, No. 3, pp. 249-265.
Herrmann et al., "The Beta-D-xylosidase of Trichoderma reesei is a multifunctional Beta-D-xylan xylohydrolase", Biochemical Journal, 1997, vol. 321, pp. 375-381 (printed in Great Britain).
Kitamoto et al., "Sequence Analysis, Overexpression, and Antisense Inhibition of a Beta-Xylosidase Gene, xylA, from Aspergillus oryzae KBN616", Applied and Environmental Microbiology, Jan. 1999, vol. 65, No. 1, pp. 20-24.
La Grange et al., "Degradation of Xylan to D-Xylose by Recombinant *Saccharomyces cerevisiae* Coexpressing the Aspergillus niger Beta-Xylosidase (xlnD) and the Trichoderma reesei Xylanase II (xyn2) Genes", Applied and Environmental Microbiology, Dec. 2001, vol. 67, No. 12, pp. 5512-5519.
Shao et al., "Characterization of a Novel Beta-Xylosidase, XylC, from Thermoanaerobacterium saccharolyticum JW/SL-YS485 ", Applied and Environmental Microbiology, Feb. 2011, vol. 77, No. 3, pp. 719-726.
Morais et al., "Functional Association of Catalytic and Ancillary Modules Dictates Enzymatic Activity in Glycoside Hydrolase Family 43 Beta-Xylosidase" Journal of Biological Chemistry, Mar. 16, 2012, vol. 287, No. 12, pp. 9213-9221.
Noguchi et al., "MetaGeneAnnotator: Detecting Species-Specific Patterns of Ribosomal Binding Site for Precise Gene Prediction in Anonymous Prokaryotic and Phage Genomes", DNA Research, pp. 387-396, 2008, vol. 15, No. 6.
Finn et al., "The Pfam protein families database", Nucleic Acids Research Database, 2010, vol. 38, p. D211-D222.
Durbin et al., 'The theory behind profile HMMs. Biological sequence analysis: probabilistic models of proteins and nucleic acids', 1998, Cambridge University Press, Cambridge, United Kingdom.

* cited by examiner

*Primary Examiner* — Yong Pak
(74) *Attorney, Agent, or Firm* — Carrier Blackman & Associates, P.C.; Joseph P. Carrier; Fulchand P. Shende

(57) ABSTRACT

A thermostable β-xylosidase including a β-xylosidase catalytic domain, the β-xylosidase catalytic domain including:
(A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-xylopyranoside as a substrate at least under conditions of a temperature of 85° C. and a pH of 6.0; or
(C) a polypeptide including an amino acid sequence having at least 80% sequence identity with the amino acid sequence represented by SEQ ID NO: 1, and having hydrolytic activity using p-nitrophenyl-β-D-xylopyranoside as a substrate at least under conditions of a temperature of 85° C. and a pH of 6.0.

1 Claim, 5 Drawing Sheets

FIG. 1

THERMOSTABLE β-XYLOSIDASE BELONGING TO GH FAMILY 3

TECHNICAL FIELD

The present invention relates to a thermostable β-xylosidase, a polynucleotide that encodes the aforementioned thermostable β-xylosidase, an expression vector for expressing the aforementioned thermostable β-xylosidase, a transformant incorporated with the aforementioned expression vector, and a method for producing a lignocellulose degradation product using the aforementioned thermostable β-xylosidase.

Priority is claimed on Japanese Patent Application No. 2014-158650, filed Aug. 4, 2014, the content of which is incorporated herein by reference.

BACKGROUND ART

In recent years, the development of alternative energy to oil is a very important issue, because of environmental problems, such as global warming and aerial pollution, in addition to the concern related to transportation energy supply. Plant biomass is the most abundant renewable energy source on earth, which is expected to serve as an alternative source to petroleum. Lignocellulose is the main component of plant biomass, and composed of polysaccharides such as celluloses and hemicelluloses (including xylan, arabinan and mannan), and lignin. These polysaccharides are hydrolyzed into monosaccharides such as glucose and xylose by a variety of glycoside hydrolases, and are used as a biofuel or a raw material of chemical products.

Lignocellulose having a complex structure is persistent and is difficult to degrade or hydrolyze with a single enzyme. For this reason, the hydrolysis of cellulose among the polysaccharides generally requires three types of enzymes: an endoglucanase of glucoside hydrolase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21). On the other hand, although the structure of hemicellulose may vary depending on the type of plants, for example, xylan is a major constituent in broad-leaved trees, herbaceous plants and the like. For the hydrolysis of xylan, it is thought that xylanase (endo-1,4-(3-xylanase, EC 3.2.1.8) and β-xylosidase (EC 3.2.1.37) are required. β-xylosidase is one of the hydrolytic enzymes associated with the process of hydrolyzing the oligosaccharides produced through the hydrolysis of hemicellulose by xylanase to produce monosaccharides.

In the conventional lignocellulose to ethanol conversion process, high-solid loading up to 30-60% in initial substrate concentration has been attempted for the purpose of higher energy efficiency and less water usage. The enzymatic hydrolysis of lignocellulose by such high-solid loading results in the high viscosity of the hydrolyzed biomass solution so that the hydrolysis of lignocellulose hardly proceeds. Therefore, for example, by carrying out the enzymatic hydrolysis process at a high temperature of 80° C. or higher using a thermostable enzyme, in addition to an increase in the hydrolysis reaction rate, since the viscosity of the hydrolyzed biomass solution also reduces, the shortening of the hydrolysis reaction time and the reduction of the amount of enzyme are expected to be achieved. For this reason, for various glycoside hydrolases, development of enzymes that are more excellent in terms of thermostability has been desired.

Many thermostable glycoside hydrolases have been obtained by isolating and identifying the thermophilic microorganisms that live in a high temperature environment, cloning the genes from these cultured and isolated microorganisms and determining the DNA sequence thereof, followed by the expression thereof using *Escherichia coli*, filamentous fungi and the like. For example, a β-xylosidase derived from filamentous fungi and a β-xylosidase derived from a filamentous fungus *Aspergillus oryzae* that exhibited an enzyme activity at a temperature of 30° C. have been disclosed in Patent Document 1 and Patent Document 2, respectively. A β-xylosidase derived from *Alicyclobacillus acidocaldarius* that exhibited an enzymatic activity at a temperature of 50° C. or higher and a pH of 5.5 or less has been disclosed in Patent Document 3. A β-xylosidase derived from *Acremonium cellulolyticus* that exhibited an enzymatic activity at a temperature of 45° C. has been disclosed in Patent Document 4. In addition, β-xylosidases isolated from certain bacteria and filamentous fungi with optimum temperatures of around 60° C. have been disclosed in Non-Patent Documents 1 to 6.

PRIOR ART DOCUMENTS

Patent Documents

[Patent Document 1] Published Japanese Translation No. Hei 11-507837 of the PCT International Publication
[Patent Document 2] Japanese Unexamined Patent Application, First Publication No. Hei 11-313683
[Patent Document 3] Published Japanese Translation No. 2011-523346 of the PCT International Publication
[Patent Document 4] Japanese Unexamined Patent Application, First Publication No. 2013-59272

Non-Patent Documents

[Non-Patent Document 1] Kormelink et al., Journal of Biotechnology, 1993, vol. 27, p. 249-265.
[Non-Patent Document 2] Herrmann et al., Biochemical Journal, 1997, vol. 321, p. 375-381.
[Non-Patent Document 3] Kitamoto et al., Applied and Environmental Microbiology, 1999, vol. 65, p. 20-24.
[Non-Patent Document 4] La Grange et al., Applied and Environmental Microbiology, 2001, vol. 67, p. 5512-5519.
[Non-Patent Document 5] Shao et al., Applied and Environmental Microbiology, 2011, vol. 77, p. 719-726.
[Non-Patent Document 6] Morais et al., Journal of Biological Chemistry, 2012, vol. 287, p. 9213-9221.

SUMMARY OF THE INVENTION

Problems to be Solved by the Invention

It is an object of the present invention to provide a novel thermostable β-xylosidase which exhibits hydrolytic activity using p-nitrophenyl-β-D-xylopyranoside (PNPX) as a substrate at least under conditions of a temperature of 85° C. and a pH of 6.0, a polynucleotide that encodes the aforementioned thermostable β-xylosidase, an expression vector for expressing the aforementioned thermostable β-xylosidase, a transformant incorporated with the aforementioned expression vector, and a method for producing a lignocellulose degradation product using the aforementioned thermostable β-xylosidase.

Means for Solving the Problem

In order to solve the above-mentioned problems, the inventors of the present invention have successfully obtained thermostable β-xylosidases having novel amino acid sequences by extracting DNA directly from hot spring high temperature soils and conducting large-scale metagenome sequencing of hardly culturable microbiota. This has led to the completion of the present invention.

That is, as the thermostable β-xylosidase, polynucleotide, expression vector, transformant, method for producing a thermostable β-xylosidase, glycoside hydrolase mixture and method for producing a lignocellulose degradation product according to the present invention, the following aspects [1] to [10] can be mentioned.

[1] A thermostable β-xylosidase including a β-xylosidase catalytic domain, the β-xylosidase catalytic domain including: (A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-xylopyranoside as a substrate at least under conditions of a temperature of 85° C. and a pH of 6.0; or
(C) a polypeptide including an amino acid sequence having at least 80% sequence identity with the amino acid sequence represented by SEQ ID NO: 1, and having hydrolytic activity using p-nitrophenyl-β-D-xylopyranoside as a substrate at least under conditions of a temperature of 85° C. and a pH of 6.0.
[2] The thermostable β-xylosidase according to the aforementioned aspect [1], which also has β-glucosidase activity.
[3] A polynucleotide including a region that encodes a β-xylosidase catalytic domain which includes: (a) a nucleotide sequence that encodes a polypeptide including an amino acid sequence represented by SEQ ID NO: 1;
(b) a nucleotide sequence that encodes a polypeptide including an amino acid sequence in which at least one amino acid is deleted, substituted, or added in the amino acid sequence represented by SEQ ID NO: 1, and having hydrolytic activity using p-nitrophenyl-β-D-xylopyranoside as a substrate at least under conditions of a temperature of 85° C. and a pH of 6.0;
(c) a nucleotide sequence that encodes a polypeptide including an amino acid sequence having at least 80% sequence identity with the amino acid sequence represented by SEQ ID NO: 1, and having hydrolytic activity using p-nitrophenyl-β-D-xylopyranoside as a substrate at least under conditions of a temperature of 85° C. and a pH of 6.0;
(d) a nucleotide sequence having at least 80% sequence identity with a nucleotide sequence represented by SEQ ID NO: 2 or 3, and encoding a polypeptide having hydrolytic activity using p-nitrophenyl-β-D-xylopyranoside as a substrate at least under conditions of a temperature of 85° C. and a pH of 6.0; or
(e) a nucleotide sequence of a polynucleotide which hybridizes with a polynucleotide including a nucleotide sequence represented by SEQ ID NO: 2 or 3 under a stringent condition, and being a nucleotide sequence that encodes a polypeptide having hydrolytic activity using p-nitrophenyl-β-D-xylopyranoside as a substrate at least under conditions of a temperature of 85° C. and a pH of 6.0.
[4] The polynucleotide according to the aforementioned aspect [3], wherein the aforementioned polypeptide also has β-glucosidase activity.
[5] An expression vector, which is incorporated with the polynucleotide according to the aforementioned aspect [3] or [4], and which is able to express a polypeptide having β-xylosidase activity in a host cell.
[6] A transformant, which is introduced with the expression vector according to the aforementioned aspect [5].
[7] The transformant according to the aforementioned aspect [6], which is a eukaryotic microbe.
[8] A method for producing a thermostable β-xylosidase, the method including a step of producing a thermostable β-xylosidase in the transformant according to the aforementioned aspect [6] or [7].
[9] A glycoside hydrolase mixture, including the thermostable β-xylosidase according to the aforementioned aspect [1] or [2], a thermostable β-xylosidase encoded by the polynucleotide according to the aforementioned aspect [3] or [4], or a thermostable β-xylosidase produced by the method for producing a thermostable β-xylosidase according to the aforementioned aspect [8], and at least one or more types of other glycoside hydrolases.
[10] A method for producing a lignocellulose degradation product, the method including producing a lignocellulose degradation product by bringing a material composed of lignocellulose containing cellulose, hemicellulose and lignin into contact with the thermostable β-xylosidase according to the aforementioned aspect [1] or [2], a thermostable β-xylosidase encoded by the polynucleotide according to the aforementioned aspect [3] or [4], the transformant according to the aforementioned aspect [6] or [7], a thermostable β-xylosidase produced by the method for producing a thermostable β-xylosidase according to the aforementioned aspect [8], or the glycoside hydrolase mixture according to the aforementioned aspect [9].

Effects of the Invention

The thermostable β-xylosidase according to the present invention has hydrolytic activity using p-nitrophenyl-β-D-xylopyranoside (hereinafter, may to be abbreviated as PNPX) as a substrate at least under conditions of a temperature of 85° C. and a pH of 6.0. For this reason, the aforementioned thermostable β-xylosidase is suitable for a hydrolysis process of materials composed of lignocellulose under high temperature conditions.

In addition, as another aspect, the aforementioned thermostable β-xylosidase is suitable for the hydrolysis process of materials containing oligosaccharides with β-xylosidic bonds under high temperature conditions.

Further, as yet another aspect, the aforementioned thermostable β-xylosidase is suitable for the hydrolysis process of an oligosaccharide with a β-xylosidic bond or a material containing an oligosaccharide with a β-glycosidic bond under high temperature conditions.

It should be noted that the aforementioned material containing an oligosaccharide with a β-xylosidic bond can be obtained, for example, by hydrolyzing lignocellulose containing hemicellulose with xylanase. The aforementioned material containing an oligosaccharide with a β-glycosidic bond can be obtained, for example, by hydrolyzing lignocellulose containing cellulose with cellobiohydrolase.

In addition, the polynucleotide, the expression vector incorporated with the aforementioned polynucleotide and the transformant introduced with the aforementioned expression vector according to the present invention are suitably used for the production of the thermostable β-xylosidase according to the present invention.

BRIEF DESCRIPTION OF THE DRAWINGS

FIG. 1 is an alignment representation of the amino acid sequence (SEQ ID NO: 1) of the catalytic domain of the β-xylosidase activity of a gene clone AR19M-346-18 and the amino acid sequence of a GH3 xylosidase (SEQ ID NO: 7) of *Fervidobacterium gondwanense*.

DESCRIPTION OF THE EMBODIMENT

[Thermostable β-Xylosidase]

Figure 2:
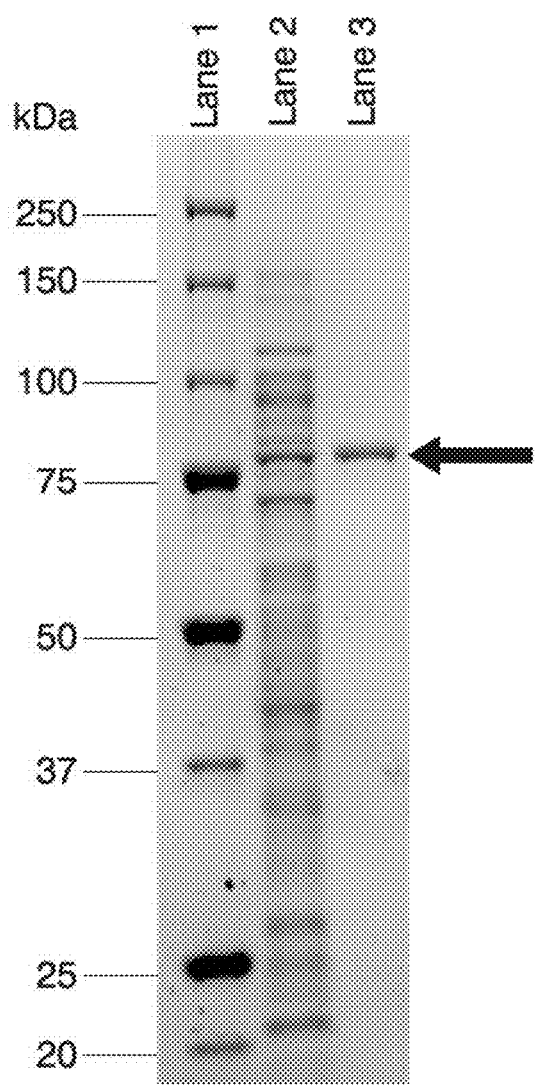
FIG. 2 is a diagram showing the results of SDS-PAGE analysis of the AR19M-346-18 protein obtained by expressing the AR19M-346-18 gene in *E. coli* in Example 1.

Many microorganisms including filamentous fungi, bacteria and archaea are difficult to culture, and about 99% of the microbes living in the microbial environments such as soil are said to be unknown microbes. In particular, the culturing of microorganisms living in high temperature environments is extremely difficult, and it is thought that merely 0.1% or less of the microorganisms living in soils have been isolated and cultured with the currently available microbial culturing techniques. This difficulty to culture such microorganisms living in high temperature soils is one factor to hinder the development of thermostable enzymes.

In recent years, because of the development of the next generation giga sequencer enabling large amount sequencing of giga base pairs, it has become possible to conduct the whole genome sequencing of the microbiota contained in soil and the like. Using this analysis technology, the metagenomic analysis method has been proposed in which the genomic DNA of a microbial group is prepared from an environmental sample such as soil, the genomes of the group having nonuniform and miscellaneous genomic organizations are directly and comprehensively sequenced, and the sequenced data are assembled by a parallel computer, so as to thereby reconstruct the genomic sequences of the microbiota. This has contributed to the rapid progress in the genome sequencing of hardly culturable microorganisms.

As shown in Example 1 described later, the inventors of the present invention extracted the genomic DNA (metagenomic DNA) of microbial groups from the collected high temperature hot spring soils (for example, hot spring water of 58 to 78° C. that contains soil, mud, microbial mats, biofilms and the like may be mentioned), and conducted shotgun sequencing and annotation of the metagenomic DNA. By so doing, 405 open reading frames (ORFs) encoding amino acid sequences similar to those of the known β-glucosidase enzymes or β-xylosidase enzymes (for example, amino acid sequences having 20% or higher sequence identity and the Expectation value (i.e. E-value) of less than $1e^{-20}$) were obtained. Of these ORFs, primers were designed based on the nucleotide sequence information of 167 full-length ORFs in which the presence of β-glucosidase catalytic domain or β-xylosidase catalytic domain could be verified, and gene candidates were cloned from the metagenomic DNA of the high temperature hot spring soils by the PCR method. The PCR-cloned DNAs were incorporated into *E. coli*, and proteins encoded by the aforementioned nucleotide sequences were expressed. These were subjected to functional screenings by assays on the PNPX degradation activity. In the end, thermostable β-xylosidases having PNPX degradation activity (hereinafter, may be referred to as "AR19M-346-18") were obtained from these ORFs. The amino acid sequence of AR19M-346-18 and the nucleotide sequence encoding the amino acid sequence of AR19M-346-18 are represented by SEQ ID NO: 1 and SEQ ID NO: 3, respectively.

As shown in Example 1 described later, AR19M-346-18 exhibited high hydrolysis activity for PNPX, and also exhibited hydrolysis activity for p-nitrophenyl-β-D-glucopyranoside (hereinafter, may be abbreviated as PNPG). On the other hand, AR19M-346-18 exhibited almost no degradation activity for phosphoric acid swollen Avicel (PSA), carboxymethyl cellulose (CMC), laminarin composed of β-1,3- and β-1,6 glucans, lichenan composed of β-1,3- and β-1,4 glucans, and Avicel which is a crystalline cellulose. From this substrate specificity, AR19M-346-18 is suggested to be a glycoside hydrolase having at least β-xylosidase activity.

It should be noted that in the present invention and the description of this application, the term "β-xylosidase activity" refers to a hydrolysis activity by using PNPX as a substrate.

In addition, in the present invention and the description of this application, the term "β-glucosidase activity" refers to a hydrolysis activity by using PNPG as a substrate.

Further, in the present invention and the description of this application, the expression "having an activity" refers to an action on at least one substrate and means that a significant difference occurs in the hydrolyzed amount of reducing ends of the substrate or the color reaction as compared to the negative control. Therefore, the expression "having β-xylosidase activity" refers to an action on at least PNPX and means that a significant difference occurs in the hydrolyzed amount of the reducing ends of the substrate or the color reaction as compared to the negative control. The expression "having β-glucosidase activity" refers to an action on at least PNPG and means that a significant difference occurs in the hydrolyzed amount of the reducing ends of the substrate or the color reaction as compared to the negative control.

The amino acid sequence of AR19M-346-18 was searched in publicly known amino acid sequence databases, resulting that the amino acid sequence showing the highest sequence identity was of a β-xylosidase (Genbank Registration ID: AFY97406.1) (SEQ ID NO: 7) belonging to the GH3 family of *Fervidobacterium gondwanense*, with sequence identity (homology) of 76%. From the substrate specificity and the sequence identity of the amino acid sequence with that of the already known proteins, it is clear that AR19M-346-18 is a novel β-xylosidase belonging to the GH3 family.

AR19M-346-18 has hydrolytic activity (that is, β-xylosidase activity) using PNPX as a substrate at least under conditions of a temperature of 85° C. and a pH of 6.0. Actually, as shown in Example 1<10> described later, AR19M-346-18 exhibits β-xylosidase activity within a temperature range from 50 to 95° C.

More specifically, the β-xylosidase activity of AR19M-346-18 tends to increase as the temperature increases in the range from 50 to 85° C. and decrease rapidly when the temperature exceeds 90° C.

Generally, in a protein having some kind of bioactivity, one or two or more amino acids can be deleted, substituted, or added, without deteriorating the bioactivity. In other words, also in AR19M-346-18, one or two or more amino acids can be deleted, substituted, or added, without causing loss of glycoside hydrolytic activity, including β-xylosidase activity.

That is, the thermostable β-xylosidase according to the present invention is a thermostable glycoside hydrolase having a β-xylosidase catalytic domain which includes any one of the following (A) to (C):
(A) a polypeptide including an amino acid sequence represented by SEQ ID NO: 1 (that is, AR19M-346-18);
(B) a polypeptide including an amino acid sequence in which at least one amino acid is deleted, substituted, or added in the amino acid sequence represented by SEQ ID NO: 1, as well as having hydrolytic activity using PNPX as a substrate at least under conditions of a temperature of 85° C. and a pH of 6.0; or
(C) a polypeptide including an amino acid sequence having at least 80% sequence identity with the amino acid sequence represented by SEQ ID NO: 1, as well as having hydrolytic activity using PNPX as a substrate at least under conditions of a temperature of 85° C. and a pH of 6.0.

In the present invention and the description of this application, a "polypeptide in which an amino acid is deleted" means that a portion of the amino acids which constitute the polypeptide has been missing (that is, removed).

In the present invention and the description of this application, a "polypeptide in which an amino acid is substituted" means that an amino acid which constitutes the polypeptide is replaced with a different amino acid.

In the present invention and the description of this application, a "polypeptide in which an amino acid is added" means that a new amino acid is inserted within the polypeptide.

In the aforementioned polypeptide of (B), the number of amino acids to be deleted, substituted, or added in the amino acid sequence represented by SEQ ID NO: 1 is preferably from 1 to 20, more preferably from 1 to 10, and still more preferably from 1 to 5.

In the aforementioned polypeptide of (C), the sequence identity with the amino acid sequence represented by SEQ ID NO: 1 is not particularly limited as long as it is 80% or greater but less than 100%, although it is preferable to be 85% or greater but less than 100%, more preferably 90% or greater but less than 100%, still more preferably 95% or greater but less than 100%, and still more preferably 98% or greater but less than 100%.

It should be noted that the sequence identity (homology) between a pair of amino acid sequences is obtained such that: two amino acid sequences are juxtaposed while having gaps in some parts accounting for insertion and deletion so that the largest numbers of corresponding amino acids can be matched, and the sequence identity is deemed to be the proportion of the matched amino acids relative to the whole amino acid sequences excluding the gaps, in the resulting alignment. The sequence identity between a pair of amino acid sequences can be obtained by using a variety of homology search software publicly known in the art. The sequence identity value between amino acid sequences in the present invention is obtained by calculation on the basis of an alignment obtained from a publicly known homology search software BLASTP.

The aforementioned polypeptides of (B) and (C) may be those that are artificially designed, or may also be homologues of AR19M-346-18 and the like, or partial proteins thereof.

The aforementioned polypeptides of (A) to (C) may be respectively synthesized in a chemical manner based on the amino acid sequence, or may also be produced by a protein expression system using the polynucleotide according to the present invention that will be described later. In addition, the aforementioned polypeptides of (B) and (C) can also be respectively synthesized artificially based on a polypeptide including the amino acid sequence represented by SEQ ID NO: 1, by using a genetic recombination technique to introduce amino acid mutation(s).

The aforementioned polypeptides of (A) to (C) have hydrolytic activities (β-xylosidase activities) using PNPX as a substrate at least under conditions of a temperature of 85° C. and a pH of 6.0. For this reason, a thermostable β-xylosidase can be obtained by having any one of the aforementioned polypeptides of (A) to (C) as the β-xylosidase catalytic domain.

The thermostable β-xylosidase according to the present invention uses PNPX as a substrate. The aforementioned thermostable β-xylosidase may also use another type of β-glucan or oligosaccharide other than PNPX as a substrate. Examples of those that can also be used as a substrate by the thermostable β-xylosidase according to the present invention include PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside; a glucan composed of β-1,3 bonds and β-1,4 bonds such as lichenan; xylan; a glucan composed of β-1,4 bonds including a crystalline cellulose, such as Avicel, a bacterial microcrystalline cellulose (BMCC) and a filter paper, a non-crystalline cellulose such as phosphoric acid swollen Avicel (PSA), and CMC; an oligosaccharide composed of β-1,4 bonds including such as cellobiose; a glucan composed of β-1,3 bonds and β-1,6 bonds such as laminarin; a glucan composed of β-1,3 bonds; a glucan composed of β-1,6 bonds and an oligosaccharide composed of β-1,6 bonds such as gentiobiose.

As the thermostable β-xylosidase according to the present invention, in addition to PNPX, a thermostable β-xylosidase that uses at least one member selected from the group consisting of PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, and p-nitrophenyl-β-D-galactopyranoside as a substrate is preferred, and a thermostable β-xylosidase that uses PNPG as a substrate is more preferred.

The thermostable β-xylosidase according to the present invention preferably exhibits hydrolytic activity (β-xylosidase activity) using PNPX as a substrate at least under conditions of a pH of 6.0 within a temperature range from 70 to 90° C., more preferably within a temperature range from 60 to 95° C. and still more preferably within a temperature range from 50 to 95° C. The optimum temperature for the thermostable β-xylosidase according to the present invention is preferably within the range from 70 to 90° C. and more preferably within the range from 80 to 90° C.

Although the optimum pH of the thermostable β-xylosidase according to the present invention varies depending on the reaction temperature, it is within a pH range from 5.0 to 7.0. As the thermostable β-xylosidase according to the present invention, those exhibiting β-xylosidase activity at least within a pH range of 4.5 to 8.0 are preferred, and those exhibiting β-xylosidase activity within a pH range of 4.0 to 8.0 are more preferred.

The thermostable β-xylosidase according to the present invention may also have a glycoside hydrolytic activity other than the β-xylosidase activity. Examples of other glycoside hydrolytic activities include endoglucanase activity, xylanase activity, β-glucosidase activity and cellobiohydrolase activity.

The thermostable β-xylosidase according to the present invention may be an enzyme solely consisting of a β-xylosidase catalytic domain which includes any one of the aforementioned polypeptides of (A) to (C), or may further include other domains. Examples of other domains include a domain present in the known β-xylosidases other than the enzyme catalytic domain. For example, the thermostable β-xylosidase according to the present invention also includes enzymes obtained by substituting an enzyme catalytic domain in a publicly known β-xylosidase with the aforementioned polypeptides of (A) to (C).

When the thermostable β-xylosidase according to the present invention includes a domain other than the β-xylosidase catalytic domain, it is also preferable to include a Fibronectin type III-like domain.

The Fibronectin type III-like domain may be either on the upstream (N-end side) or the downstream (C-end side) of the β-xylosidase catalytic domain. In addition, the Fibronectin type III-like domain and β-xylosidase catalytic domain may be directly linked, or linked via a linker domain of an appropriate length. The thermostable β-xylosidase according to the present invention is preferably such that the Fibronectin type III-like domain is present on the upstream or the downstream of the β-xylosidase catalytic domain via a linker domain, more preferably such that the Fibronectin type III-like domain is present on the downstream of the β-xylosidase catalytic domain via a linker domain.

In addition, the thermostable β-xylosidase according to the present invention may also have a signal peptide enabling to transport it to a specific region to effect localization within a cell, or a signal peptide to effect extracellular secretion, at the N end or the C end. Such a signal peptide can be exemplified by an apoplastic transport signal peptide, an endoplasmic reticulum retention signal peptide, a nuclear transport signal peptide, a secretory signal peptide, or the like. The endoplasmic reticulum retention signal peptide can be exemplified by, for example, a signal peptide including a HDEL amino acid sequence, or the like. In those cases where the thermostable β-xylosidase according to the present invention has a signal peptide at the N end or the C end, the thermostable β-xylosidase expressed in a transformant can be secreted outside the cell, or can be localized in the intracellular endoplasmic reticulum, or the like.

In addition, the thermostable β-xylosidase according to the present invention may also be added with, for example, various types of tags at the N end or the C end of the thermostable β-xylosidase, so as to enable easy and convenient purification in a case of the production using an expression system. Regarding such a tag, for example, it is possible to use a tag for usual use in the expression or purification of a recombinant protein, such as a His tag, a HA (hemagglutinin) tag, a Myc tag, and a Flag tag.

[Polynucleotide that Encodes Thermostable β-Xylosidase]

A polynucleotide according to the present invention encodes a thermostable β-xylosidase according to the present invention. The aforementioned thermostable β-xylosidase can be produced by using the expression system of a host made by introducing an expression vector incorporated with the polynucleotide into the host.

More specifically, the polynucleotide according to the present invention is a polynucleotide having a region that encodes a β-xylosidase catalytic domain which includes any one of the following nucleotide sequences (a) to (e).

(a) A nucleotide sequence that encodes a polypeptide including the amino acid sequence represented by SEQ ID NO: 1;
(b) A nucleotide sequence that encodes a polypeptide including an amino acid sequence in which at least one amino acid is deleted, substituted, or added in the amino acid sequence represented by SEQ ID NO: 1, as well as having hydrolytic activity using PNPX as a substrate at least under conditions of a temperature of 85° C. and a pH of 6.0;
(c) A nucleotide sequence that encodes a polypeptide including an amino acid sequence having at least 80% sequence identity with the amino acid sequence represented by SEQ ID NO: 1, as well as having hydrolytic activity using PNPX as a substrate at least under conditions of a temperature of 85° C. and a pH of 6.0;
(d) A nucleotide sequence having at least 80% sequence identity with a nucleotide sequence represented by SEQ ID NO: 2 or 3, as well as encoding a polypeptide having hydrolytic activity using PNPX as a substrate at least under conditions of a temperature of 85° C. and a pH of 6.0; or
(e) A nucleotide sequence of a polynucleotide which hybridizes with a polynucleotide including a nucleotide sequence represented by SEQ ID NO: 2 or 3 under a stringent condition, as well as being a nucleotide sequence that encodes a polypeptide having hydrolytic activity using PNPX as a substrate at least under conditions of a temperature of 85° C. and a pH of 6.0.

It should be noted that in the present invention and the description of this application, a "polynucleotide in which a nucleotide is deleted" means that a portion of the nucleotides which constitute the polynucleotide is missing (that is, removed).

In the present invention and the description of this application, a "polynucleotide in which a nucleotide is substituted" means that a nucleotide which constitutes the polynucleotide is replaced with a different nucleotide.

In the present invention and the description of this application, a "polynucleotide in which a nucleotide is added" means that a new nucleotide is inserted within the polynucleotide.

In the present invention and the description of this application, the term "under a stringent condition" can be exemplified by the method described in Molecular Cloning—A Laboratory Manual Third Edition (Sambrook et al., Cold Spring Harbor Laboratory Press). The example thereof includes a condition in which hybridization is performed by incubation in a hybridization buffer including 6×SSC (composition of 20×SSC: 3M sodium chloride, 0.3M citric acid solution, and pH7.0), 5×Denhardt's solution (composition of 100×Denhardt's solution: 2 mass % bovine serum albumin, 2 mass % Ficoll, 2 mass % polyvinylpyrrolidone), 0.5 mass % SDS, 0.1 mg/mL salmon sperm DNA, and 50% formamide, at a temperature of 42 to 70° C. for several hours to overnight. The washing buffer for use in the washing after the incubation is preferably 1×SSC solution containing 0.1 mass % SDS, and more preferably 0.1×SSC solution containing 0.1 mass % SDS.

In the aforementioned nucleotide sequences of (a) to (e), it is preferable to select a degenerate codon having high frequency of usage in the host. For example, the aforementioned nucleotide sequence of (a) may be a nucleotide sequence represented by SEQ ID NO: 2, may be a nucleotide sequence represented by SEQ ID NO: 3, or may be a nucleotide sequence altered to have a codon having high frequency of usage in the host without changing the amino acid sequence to be encoded by the nucleotide sequence represented by SEQ ID NO: 2 or 3. Note that, these codons can be altered by a publicly known gene sequence modification technique or artificial gene synthesis.

The polynucleotide including the nucleotide sequence represented by SEQ ID NO: 2 or 3 may be synthesized in a chemical manner based on the nucleotide sequence information, or may be obtained as a full length of a gene that encodes AR19M-346-18 (may be referred to as "AR19M-346-18 gene") or a partial region thereof including the β-xylosidase catalytic domain (for example, in SEQ ID NO: 1, a region encoding a partial region composed of 325 amino acids from threonine at position 23 to valine at position 347, a region encoding a partial region composed of 260 amino acids from isoleucine at position 379 to threonine at position 638, or a region encoding a partial region composed of 616 amino acids from threonine at position 23 to threonine at position 638) from the natural world by using a genetic recombination technique. The full length of the AR19M-346-18 gene or the partial region thereof can be obtained by, for example, collecting a sample containing microorganisms from the natural world, and conducting PCR using the genomic DNA recovered from the sample as a template, with a forward primer and a reverse primer designed on the basis of the nucleotide sequence represented by SEQ ID NO: 2 or 3 by a conventional method. The cDNA synthesized by a reverse transcription reaction using mRNA recovered from the sample as a template may also be used as a template. Note that, it is preferable that the sample for recovering the nucleic acid serving as a template is a sample collected from a high temperature environment such as hot spring soil.

In the aforementioned nucleotide sequence of (d), the sequence identity with the nucleotide sequence represented by SEQ ID NO: 2 or 3 is not particularly limited as long as it is 80% or greater but less than 100%, although it is preferable to be 85% or greater but less than 100%, more preferably 90% or greater but less than 100%, and still more preferably 95% or greater but less than 100%.

Note that, the sequence identity (homology) between a pair of nucleotide sequences is obtained such that: two nucleotide sequences are juxtaposed while having gaps in some parts accounting for insertion and deletion so that the largest numbers of corresponding nucleotides can be matched, and the sequence identity is deemed to be the proportion of the matched nucleotides relative to the whole nucleotide sequences excluding gaps, in the resulting alignment. The sequence identity between a pair of nucleotide sequences can be obtained by using a variety of homology search software publicly known in the art. The sequence identity value between nucleotide sequences in the present invention is obtained by calculation on the basis of an alignment obtained from a publicly known homology search software BLASTN.

For example, the polynucleotide including the aforementioned nucleotide sequence of (b), (c), or (d) can be respectively synthesized artificially by deleting, substituting, or adding one or two or more nucleotides in a polynucleotide including the nucleotide sequence represented by SEQ ID NO: 2 or 3. In addition, the aforementioned nucleotide sequence of (b), (c), or (d) may also be a full length sequence of a homologous gene of the AR19M-346-18 gene or a partial sequence thereof. The homologous gene of the AR19M-346-18 gene can be obtained by a genetic recombination technique for use in obtaining a homologous gene of a gene whose nucleotide sequence has been already known.

The polynucleotide according to the present invention may have only the region that encodes the β-xylosidase catalytic domain, or may also have a region that encodes a cellulose-binding module, a linker sequence, various types of signal peptides, various types of tags, or the like, in addition to the aforementioned region.

[Expression Vector]

The expression vector according to the present invention is incorporated with the aforementioned polynucleotide according to the present invention, and is able to express a polypeptide having hydrolytic activity using PNPX as a substrate at least under conditions of a temperature of 85° C. and a pH of 6.0 in a host cell. That is, it is an expression vector which is incorporated with the aforementioned polynucleotide according to the present invention in a state where the aforementioned thermostable β-xylosidase according to the present invention can be expressed. More specifically, it is necessary for the expression vector to be incorporated with an expression cassette including, from the upstream, DNA having a promoter sequence, the aforementioned polynucleotide according to the present invention, and DNA having a terminator sequence. It should be noted that the incorporation of the polynucleotide into the expression vector can be performed by using a well-known genetic recombination technique. It is also possible to use a commercially available expression vector preparation kit for the incorporation of the polynucleotide into the expression vector.

In the present invention and the description of this application, an "expression vector" is a vector including, from upstream, DNA having a promoter sequence, DNA having a sequence for incorporating foreign DNA, and DNA having a terminator sequence.

The expression vector may be a vector to be introduced into a prokaryotic cell such as E. coli, or to be introduced into a eukaryotic cell such as a yeast, a filamentous fungus, a cultured insect cell, a cultured mammalian cell, or a plant cell. Regarding such an expression vector, an arbitrary expression vector for usual use can be adopted corresponding to the respective host.

It is preferable that the expression vector according to the present invention is an expression vector incorporated with not only the aforementioned polynucleotide according to the present invention but also a drug resistance gene or the like. This is because it makes it easy to screen cells transformed by the expression vector and untransformed cells.

The drug resistance gene can be exemplified by a kanamycin resistance gene, a hygromycin resistance gene, a bialaphos resistance gene, or the like.

[Transformant]

The transformant according to the present invention is introduced with the above-mentioned expression vector according to the present invention. In the aforementioned transformant, the above-mentioned thermostable β-xylosidase according to the present invention can be expressed. The host to introduce the expression vector may be a prokaryotic cell such as E. coli or a eukaryotic cell such as a yeast, a filamentous fungus, a cultured insect cell, a cultured mammalian cell, or a plant cell. That is, the transformant according to the present invention is E. coli, a yeast, a filamentous fungus, a cultured insect cell, a cultured mammalian cell, a plant cell, or the like which is introduced with the expression vector according to the present invention.

By culturing a transformant of *E. coli*, the thermostable β-xylosidase according to the present invention can be produced more easily and conveniently with high yield. On the other hand, because proteins are hydrolyzed in eukaryotic cells, a thermostable β-xylosidase which is more thermostable can be produced by using a transformant of a eukaryotic cell rather than by using a transformant of a prokaryotic cell.

The method to produce the transformant using the expression vector is not particularly limited, and a method for usual use in the production of transformants can be conducted. The concerned method can be exemplified by a heat shock method, an *Agrobacterium*-mediated method, a particle gun method, an electroporation method, a PEG (polyethylene glycol) method, and the like. Of these, if the host is a plant cell, a particle gun method or an *Agrobacterium*-mediated method is preferred.

If a prokaryotic cell, a yeast, a filamentous fungus, a cultured insect cell, a cultured mammalian cell, or the like is used as a host, the obtained transformant is generally able to be cultured by a usual method in the same manner as that of the untransformed host.

[Method for Producing a Thermostable β-Xylosidase]

The method for producing a thermostable β-xylosidase according to the present invention is a method to produce a thermostable β-xylosidase in the aforementioned transformant according to the present invention. When culturing a transformant produced by using the expression vector incorporated with the aforementioned polynucleotide according to the present invention on the downstream of a promoter which has no ability to regulate the timing of the expression or the like, in the transformant, the thermostable β-xylosidase according to the present invention is expressed constitutively. On the other hand, for the transformant produced by using a so-called expression inducible promoter to induce the expression by means of a specific compound, temperature condition, or the like, the thermostable β-xylosidase is expressed in the concerned transformant by culturing the transformant and conducting an induction treatment suitable for the respective expression-inducing condition.

The thermostable β-xylosidase produced by the transformant may be used in a state of being retained in the transformant, or may be extracted/purified from the transformant.

The method to extract or purify the thermostable β-xylosidase from the transformant is not particularly limited as long as the method does not deteriorate the activity of the thermostable β-xylosidase, and the extraction can be done by a method for usual use in the extraction of a polypeptide from cells or biological tissues. The method can be exemplified by a method in which the transformant is immersed in an appropriate extraction buffer to extract the thermostable β-xylosidase, and thereafter the liquid extract and the solid residue are separated. The extraction buffer preferably contains a solubilizing agent such as a surfactant. If the transformant is a plant, the transformant may be previously shredded or crushed before immersing in an extraction buffer. Moreover, as the method for separating the liquid extract and the solid residue, for example, a publicly known solid-liquid separation treatment such as a filtration method, a compression filtration method, or a centrifugation treatment method may be used, or the transformant immersed in an extraction buffer may be squeezed. The thermostable β-xylosidase in the liquid extract can be purified by using a publicly known purification method such as a salting-out method, an ultrafiltration method, or a chromatography method.

If the thermostable β-xylosidase according to the present invention is expressed in a state of having a secretory signal peptide in a transformant, a solution containing the thermostable β-xylosidase can be easily and conveniently obtained by culturing the transformant and thereafter recovering a culture liquid supernatant made by removal of the transformant from the obtained culture product. Moreover, if the thermostable β-xylosidase according to the present invention has a tag such as a His tag, the thermostable β-xylosidase in a liquid extract or in a culture supernatant can be easily and conveniently purified by an affinity chromatography method using the tag.

In other words, the method for producing a thermostable β-xylosidase according to the present invention includes culturing the transformant according to the present invention and producing a thermostable β-xylosidase within the transformant according to the present invention, and, according to need, extracting and purifying the thermostable β-xylosidase from the transformant.

[Glycoside Hydrolase Mixture]

The glycoside hydrolase mixture according to the present invention can also be used as a glycoside hydrolase mixture containing the aforementioned thermostable β-xylosidase according to the present invention, or a thermostable β-xylosidase produced by the aforementioned method for producing a thermostable β-xylosidase according to the present invention, and at least one or more types of other glycoside hydrolases. The thermostable β-xylosidase produced by the aforementioned method for producing a thermostable β-xylosidase according to the present invention may be in a state of being included in the transformant, or may be extracted or purified from the transformant. By using the thermostable β-xylosidase according to the present invention as a mixture with other glycoside hydrolases in the reaction to hydrolyze polysaccharides, persistent lignocelluloses can be more efficiently degraded.

The other glycoside hydrolase than the aforementioned thermostable β-xylosidase to be contained in the glycoside hydrolase mixture is not particularly limited as long as it has lignocellulose hydrolysis activity. The other glycoside hydrolase than the aforementioned β-xylosidase to be contained in the glycoside hydrolase mixture can be exemplified by hemicellulases such as xylanase, cellobiohydrolase, β-glucosidase, endoglucanase, or the like. In addition to the thermostable β-xylosidase, the glycoside hydrolase mixture according to the present invention is preferably a mixture containing at least either one of glycoside hydrolases (i.e., a hemicellulase or an endoglucanase), and more preferably a mixture containing both of glycoside hydrolases (i.e., a hemicellulase and an endoglucanase). Among them, a mixture containing at least one type of glycoside hydrolases selected from the group consisting of xylanase, β-xylosidase, cellobiohydrolase, and endoglucanase is still more preferred; and a mixture containing all of glycoside hydrolases (i.e., xylanase, β-xylosidase, cellobiohydrolase, and endoglucanase) is particularly preferred.

The other glycoside hydrolase to be contained in the glycoside hydrolase mixture is preferably a thermostable glycoside hydrolase having glycoside hydrolase activity at least at a temperature of 85° C., and more preferably a thermostable glycoside hydrolase having glycoside hydrolase activity at a temperature of 70 to 90° C. When all the enzymes contained in the glycoside hydrolase mixture are thermostable (for example, the optimum temperature of the enzyme activity or the thermal denaturation temperature of the enzyme protein is 70° C. or higher), the reaction to degrade lignocelluloses with the glycoside hydrolase mixture can be efficiently conducted under a high temperature condition. That is, if the glycoside hydrolase mixture contains only thermostable glycoside hydrolases, it becomes possible, by using the glycoside hydrolase mixture for a lignocellulose hydrolysis process, to conduct the lignocellulose hydrolysis reaction under a high temperature environment where the hydrolysis temperature is from 70 to 90° C. (high temperature hydrolysis). With this high temperature hydrolysis, the amount of enzymes and the time for hydrolysis can be remarkably reduced, and the cost for hydrolysis can be largely cut out.

[Method for Producing a Lignocellulose Degradation Product]

The method for producing a lignocellulose degradation product according to the present invention is a method to obtain a lignocellulose degradation product, including hydrolyzing an oligosaccharide produced by the hydrolysis of hemicellulose with xylanase or an oligosaccharide produced by the hydrolysis of cellulose with cellobiohydrolase to monosaccharides with the thermostable β-xylosidase according to the present invention.

As lignocellulose degradation product, for example, monosaccharide such as glucose and xylose can be mentioned.

Another aspect of the method for producing a lignocellulose degradation product according to the present invention is a method in which a material containing an oligosaccharide having a β-xylosidic bond is hydrolyzed with the thermostable β-xylosidase according to the present invention to thereby produce a lignocellulose degradation product including a degradation product of the oligosaccharide.

Yet another aspect of the method for producing a lignocellulose degradation product according to the present invention is a method in which a material containing an oligosaccharide having a β-glycosidic bond is hydrolyzed with the thermostable β-xylosidase according to the present invention to thereby produce a lignocellulose degradation product including a degradation product of the oligosaccharide.

It should be noted that the aforementioned material containing an oligosaccharide with a β-xylosidic bond can be obtained, for example, by hydrolyzing lignocellulose containing hemicellulose with xylanase. The aforementioned material containing an oligosaccharide with a β-glycosidic bond can be obtained, for example, by hydrolyzing lignocellulose containing cellulose with cellobiohydrolase. More specifically, the method for producing a lignocellulose degradation product according to the present invention is a method, including producing a hemicellulose or cellulose degradation product by bringing a material composed of lignocellulose, more specifically, a material composed of lignocellulose containing hemicellulose or cellulose, into contact with the thermostable β-xylosidase according to the present invention, the transformant according to the present invention, the thermostable β-xylosidase produced by the method for producing a thermostable β-xylosidase according to the present invention, or the glycoside hydrolase mixture according to the present invention.

As another aspect of the method for producing a lignocellulose degradation product according to the present invention, more specifically, it is a method, including bringing a material containing an oligosaccharide with a β-xylosidic bond into contact with the thermostable β-xylosidase according to the present invention, the transformant according to the present invention, the thermostable β-xylosidase produced by the method for producing a thermostable β-xylosidase according to the present invention, or the glycoside hydrolase mixture according to the present invention, thereby producing a degradation product of the oligosaccharide.

As yet another aspect of the method for producing a lignocellulose degradation product according to the present invention, more specifically, it is a method, including bringing a material containing an oligosaccharide with a β-glycosidic bond into contact with the thermostable β-xylosidase according to the present invention, the transformant according to the present invention, the thermostable β-xylosidase produced by the method for producing a thermostable β-xylosidase according to the present invention, or the glycoside hydrolase mixture according to the present invention, thereby producing a degradation product of the oligosaccharide.

The aforementioned material containing an oligosaccharide with a β-xylosidic bond may be prepared by hydrolyzing lignocellulose containing hemicellulose with xylanase, and the aforementioned material containing an oligosaccharide with a β-glycosidic bond may be prepared by hydrolyzing lignocellulose containing cellulose with cellobiohydrolase.

The material composed of lignocellulose containing hemicellulose or cellulose is not particularly limited as long as it contains hemicellulose or cellulose. Such a material can be exemplified by cellulosic biomass such as a weed and an agricultural waste, used paper, or the like. The above material is preferably subjected to a physical treatment such as crushing or shredding, a chemical treatment with an acid, alkali, or the like, or a treatment such as immersing in an appropriate buffer or a dissolution treatment, or the like, prior to being brought into contact with the thermostable β-xylosidase according to the present invention.

That is, the method for producing a lignocellulose degradation product according to the present invention may further include a step in which the aforementioned material composed of lignocellulose containing hemicellulose or cellulose is subjected to a physical treatment, a chemical treatment, or an immersion treatment in a buffer or a dissolution treatment, prior to being brought into contact with the thermostable β-xylosidase according to the present invention.

The reaction condition of the hydrolysis reaction of hemicellulose by means of the thermostable β-xylosidase according to the present invention may suffice if the condition allows the thermostable β-xylosidase to exhibit cellooligosaccharide hydrolysis activity. For example, it is preferable to conduct the reaction at a temperature of 60 to 90° C. and a pH of 5.0 to 9.0, more preferable to conduct the reaction at a temperature of 70 to 90° C. and a pH of 5.0 to 9.0, and still more preferable to conduct the reaction at a temperature of 70 to 90° C. and a pH of 6.0 to 8.5. The reaction time of the hydrolysis reaction is appropriately adjusted in consideration of the type, the method of pretreatment, the amount, or the like, of the material to be supplied to the hydrolysis. For example, the hydrolysis reaction can be carried out in a reaction time of 10 minutes to 100 hours, and 1 to 100 hours when degrading a material containing a cellulose-based biomass.

For the hydrolysis reaction of lignocellulose, it is also preferable to use at least one or more types of other glycoside hydrolases, in addition to the thermostable β-xylosidase according to the present invention. The other glycoside hydrolase may be the same as the glycoside hydrolase that can be contained in the aforementioned glycoside hydrolase mixture, and it is preferable to be a thermostable glycoside hydrolase having glycoside hydrolase activity at least at a temperature of 85° C., and preferably at least at a temperature of 70 to 90° C. In addition, one aspect of the method for producing a lignocellulose degradation product is the use of the thermostable β-xylosidase according to the present invention, the transformant according to the present invention, or a thermostable β-xylosidase produced by the method for producing a thermostable β-xylosidase according to the present invention, and another aspect is the use of the aforementioned glycoside hydrolase mixture.

EXAMPLES

Next is a more detailed description of the present invention with reference to Examples. However, the present invention is not to be limited to the following Examples.

Example 1

Cloning of Novel Thermostable β-Xylosidase from Hot Spring Soil

<1> DNA Extraction from Hot Spring Soil and Whole Genome Sequencing (WGS)

With the purpose of searching for genes of novel thermostable β-xylosidase exhibiting activity at a temperature of 70 to 90° C., soil DNA was collected from neutral to weakly alkaline hot springs and subjected to nucleotide sequencing of the metagenomic DNA of the microbiota constituting the soil.

As the soil sample from neutral to weakly alkaline hot springs, hot spring water containing soil, clay, and biomat was collected from five sampling points having gushing high temperature outdoor hot springs in three areas in Japan (metagenomic DNA samples N2, AR19, AR15, OJ1, and H1). These hot spring soil samples were within a range of temperature from 58 to 78° C. and a pH of 7.2 to 8 at the time of the collection.

DNA was extracted from 10 g of the collected hot spring soil samples by using the DNA extraction kit (ISOIL Large for Beads ver.2, manufactured by NIPPON GENE Co., Ltd.). The extracted DNA was subjected to shotgun sequencing of the metagenomic DNA by using the GS FLX Titanium 454 sequencer manufactured by Roche Diagnostics K.K. and the HiSeq 2000 sequencer manufactured by Illumina, Inc. 5 μg of the extracted DNA and the product amplified by using the genomic DNA amplification kit (GenomiPhi V2 DNA Amplification Kit, manufactured by GE Healthcare) were subjected to the metagenomic DNA sequencing using the 454 sequencer and the HiSeq 2000 sequencer, respectively. In the sequencing by the HiSeq 2000 sequencer, DNA libraries and reagents were poured into the flow cell using the cBot manufactured by Illumina, Inc., to automatically form a cluster having the identical sequence within the flow cell from a single DNA molecule. Paired-end sequencing of 101 by was conducted using the HiSeq 2000 sequencer to obtain metagenomic sequence data.

The metagenomic DNA sequencing was carried out using the hot spring soil sample AR19. By so doing, a data set of the whole genome sequence (WGS) was obtained in which an average read length of 396 bp, a total number of reads of 2,766,332, and a total quantity of sequenced genomes of 1,106,243,280 by were obtained with the 454 sequencer, and an average read length of 92.65 by in paired-end reads, a total number of reads of 894,238,096, and a total quantity of sequenced genomes of 83,112,168,755 by were obtained with the HiSeq 2000 sequencer, resulting in a total of 84.2 Gbp.

<2> Assembling and Statistics of Hot Spring Metagenomic Data

The nucleotide sequence that has been read in the 454 sequencer and the HiSeq 2000 sequencer was subjected to quality filtering and de novo assembly by using the CLC Genomics Workbench (ver. 5.5.1) manufactured by CLC bio. After the quality filtering, the total read length obtained with the 454 sequencer reached 2,766,328 bp, and the total read length of the nucleotide sequence data obtained with the HiSeq 2000 sequencer reached 81,323,692,563 bp. After the assembly, the number of contigs with a length of more than 500 by was 967,925, and the overall length reached 419,787,603 bp. Of these, the longest contig length was 287,641 bp.

<3> Prediction of Open Reading Frames (ORFs) of β-Xylosidase

The sequences of EC numbers of 3.2.1.4 (cellulase), 3.2.1.21 (β-glucosidase), 3.2.1.37 (β-xylosidase), 3.2.1.91 (cellulose 1,4-β-cellobiosidase), and 3.2.1.8 (endo 1,4-β-xylanase) were downloaded from the UniProt database (http://www.uniprot.org/) (the date of access: 2011/12/9), and the proteome local database of these glycoside hydrolase genes was constructed. Using the annotation software Metagene (Noguchi et al., DNA Research, 2008, 15(6)), gene regions (=open reading frames) were predicted from the contig sequences obtained from the above-mentioned process <2> (Metagene option: −m). In order to extract the glycoside hydrolase gene from the predicted ORF, the aforementioned local database using BLASTP (blastall ver. 2.2.18) was referred to. Optional conditions of BLASTP were set such that: "Filter query sequence=false", "Expectation value (E)<1e-20" [hereunder, the default values: Cost to open a gap=−1, Cost to extended gap=−1, X dropoff value for gapped alignment=0, Threshold for extending hits=0, and Word size=default], and the hit ORF sequences were collected as glycoside hydrolase genes. The collected nucleotide sequences included the genes of glycoside hydrolases such as cellulases, endohemicellulases, and debranching enzymes.

<4> Classification of Genes into Glycoside Hydrolase (GH) Families

The nucleotide sequences that had been collected in the above-mentioned process <3> were subjected to functional classification, with reference to the protein functional region sequence database of pfam HMMs (Pfam version 23.0 and HMMER v2.3; Finn et al., Nucleic Acids Research Database, 2010, Issue 38, p. D211-222). More specifically, the glycoside hydrolase (GH) families were determined for each of the nucleotide sequences that had been collected in the above-mentioned process <3> by the homology with the Pfam domain database by using the protein motif search program HMMER (Durbin et al., "The theory behind profile HMMs. Biological sequence analysis: probabilistic models of proteins and nucleic acids", 1998, Cambridge University Press.; hmmpfam (Ver.2.3.2), E-value cutoff <1e$^{-5}$; Database=Pfam_fs (models that can be used to find fragments of the represented domains in a sequence)). It should be noted that those that covered 70% or more of the sequence of GH catalytic domain were counted as enzyme genes belonging to the respective families.

From the sequence data of metagenome AR19 with a length of 84.2 Gbp, 602,589 ORFs were predicted by Metagene, and the number of full-length ORFs was 251,146.

406 ORFs hit as the β-glucosidase or β-xylosidase sequence by the homology search with BLASTP. Out of these 406 ORFs, 168 ORFs were predicted to be β-glucosidase genes or β-xylosidase genes by pfam HMMs, whereas 238 ORFs either exhibited a coverage of the GH catalytic domain sequence of less than 70%, or did not hit any sequence in the pfam database.

The result of the GH family classification of 168 ORFs predicted as (3-glucosidase genes or β-xylosidase genes is shown in Table 1. The sequences exhibiting a coverage of the GH catalytic domain of less than 70% and the sequences whose homologues could not be found in the Pfam database were classified as unknown GH. As shown in Table 1, among the ORFs predicted as β-glucosidase or β-xylosidase, 19 full-length ORFs belonging to the GH1 family, 57 full-length ORFs belonging to the GH3 family, 13 full-length ORFs belonging to the GH31 family, and 13 full-length ORFs belonging to the GH43 family were obtained from the metagenome AR19. Primers were designed for all of these full-length ORFs having been predicted as β-glucosidase genes or β-xylosidase genes, and these genes were cloned from the hot spring soil metagenomic DNA by PCR. As a result, a β-xylosidase gene was isolated from the open reading frame AR19M-346 belonging to the GH3 family and having a xylosidase sequence.

TABLE 1

| AR19 metagenome | GH family classification of β-glucosidase or β-xylosidase genes | | | | | |
|---|---|---|---|---|---|---|
| | GH1 | GH3 | GH31 | GH43 | Other GH families | Total |
| Full-length ORFs | 19 | 57 | 13 | 13 | 3 | 105 |
| Incomplete ORFs | 3 | 52 | 4 | 4 | 0 | 63 |
| Total number of ORFs | 22 | 109 | 17 | 17 | 3 | 168 |

<5> Open Reading Frame AR19M-346

The open reading frame AR19M-346 encoded a polypeptide (SEQ ID NO: 1) including 773 amino acid residues and was a full-length sequence (SEQ ID NO: 2), such that the polypeptide started from methionine which was an amino acid residue at position 1, and the 3' end of the nucleotide sequence encoding the polypeptide ended with a termination codon. From the sequence homology of motifs, it was predicted that the polypeptide encoded by the open reading frame AR19M-346 was a multi-domain protein constituted of the N-terminal side domain of the catalytic domain of the Glycoside hydrolase family 3 which was composed of 325 amino acids from threonine (T) at position 23 to valine (V) at position 347; the C-terminal side domain of the catalytic domain of the Glycoside hydrolase family 3 which was composed of 260 amino acids from isoleucine (I) at position 379 to threonine (T) at position 638; and the Fibronectin type III-like domain which was composed of 70 amino acids from glutamic acid (E) at position 673 to serine (S) at position 742. According to analysis using the signal sequence prediction software SignalP 4.1, the amino acid sequence from methionine (M) at position 1 serving as the initiation codon to the amino acid at position 22 did not encode a secretion signal, and the function thereof was unknown.

<6> Gene Cloning

PCR was conducted using a hot spring soil DNA that had been amplified by the genomic DNA amplification kit (GenomiPhi V2 DNA Amplification Kit, manufactured by GE Healthcare) as a template, and by using a forward primer composed of the nucleotide sequence represented by SEQ ID NO: 6 (5'-CACCATGGAGATTTATAAGGATCCA-3': obtained by adding 4 nucleotides (CACC) to the 5'-end side of the nucleotide sequence represented by SEQ ID NO: 4. The nucleotides CACC added on the 5' side is a sequence for insertion into a vector) and a reverse primer composed of the nucleotide sequence represented by SEQ ID NO: 5 (5'-TTATATAATTTTAACCTCGGTAAAGAATATCCTTT-3'). The nucleotide sequence represented by SEQ ID NO: 4 is a nucleotide sequence which is homologous (identical) with a partial sequence including the nucleotides at position 1 to 21 of the nucleotide sequence represented by SEQ ID NO: 2 or 3. Moreover, the nucleotide sequence represented by SEQ ID NO: 5 is a nucleotide sequence which is complementary with a partial sequence including the nucleotides at position 2288 to 2322 of the nucleotide sequence represented by SEQ ID NO: 2 or 3. The amplified PCR products were inserted in the pET101/D-TOPO vector of Champion pET Directional TOPO Expression Kits (manufactured by Life Technologies), and transformed into the One Shot TOP10 strain. Positive clones were selected by colony PCR, and then cultured in a LB liquid medium containing 100 mg/L ampicillin at a temperature of 37° C. and 200 rpm for 17 to 20 hours, followed by the preparation of plasmids using the miniprep kit (Wizard plus SV Minipreps DNA Purification System, manufactured by Promega). The prepared plasmids were sequenced by using the 3730 DNA Analyzer sequencer of Life Technologies.

Two gene clones AR19M-346-18 and AR19M-346-43 were obtained from the open reading frame AR19M-346 by PCR cloning. The nucleotide sequence of the gene clone AR19M-346-18 (SEQ ID NO: 3) which was a β-xylosidase candidate gene contained 2322 by like that of the open reading frame AR19M-346 (SEQ ID NO: 2), and was different from the predicted ORF by one nucleotide. That is, the nucleotide at position 1653 was cytosine (C) in the cloned gene (SEQ ID NO: 3), whereas it was thymine (T) in the predicted ORF (SEQ ID NO: 2). However, no difference was observed between the amino acid sequences (SEQ ID NO: 1) to be encoded by them.

The polypeptide (AR19M-346-18) encoded by the β-xylosidase candidate gene AR19M-346-18 (hereinafter, referred to as a "AR19M-346-18 gene") is composed of 773 amino acids, and includes the same amino acid sequence as that of the polypeptide encoded by the open reading frame AR19M-346 which was composed of 773 amino acid residues (SEQ ID NO: 1). AR19M-346-18 was a multi-domain protein constituted of the N-terminal side domain of the catalytic domain of the Glycoside hydrolase family 3 which was composed of 325 amino acids from threonine at position 23 to valine at position 347 (T23-V347); the C-terminal side domain of the catalytic domain of the Glycoside hydrolase family 3 which was composed of 260 amino acids from isoleucine at position 379 to threonine at position 638 (I379-T638); and the Fibronectin type III-like domain which was composed of 70 amino acids from glutamic acid at position 673 to serine at position 742 (E673-S742).

Figure 1:
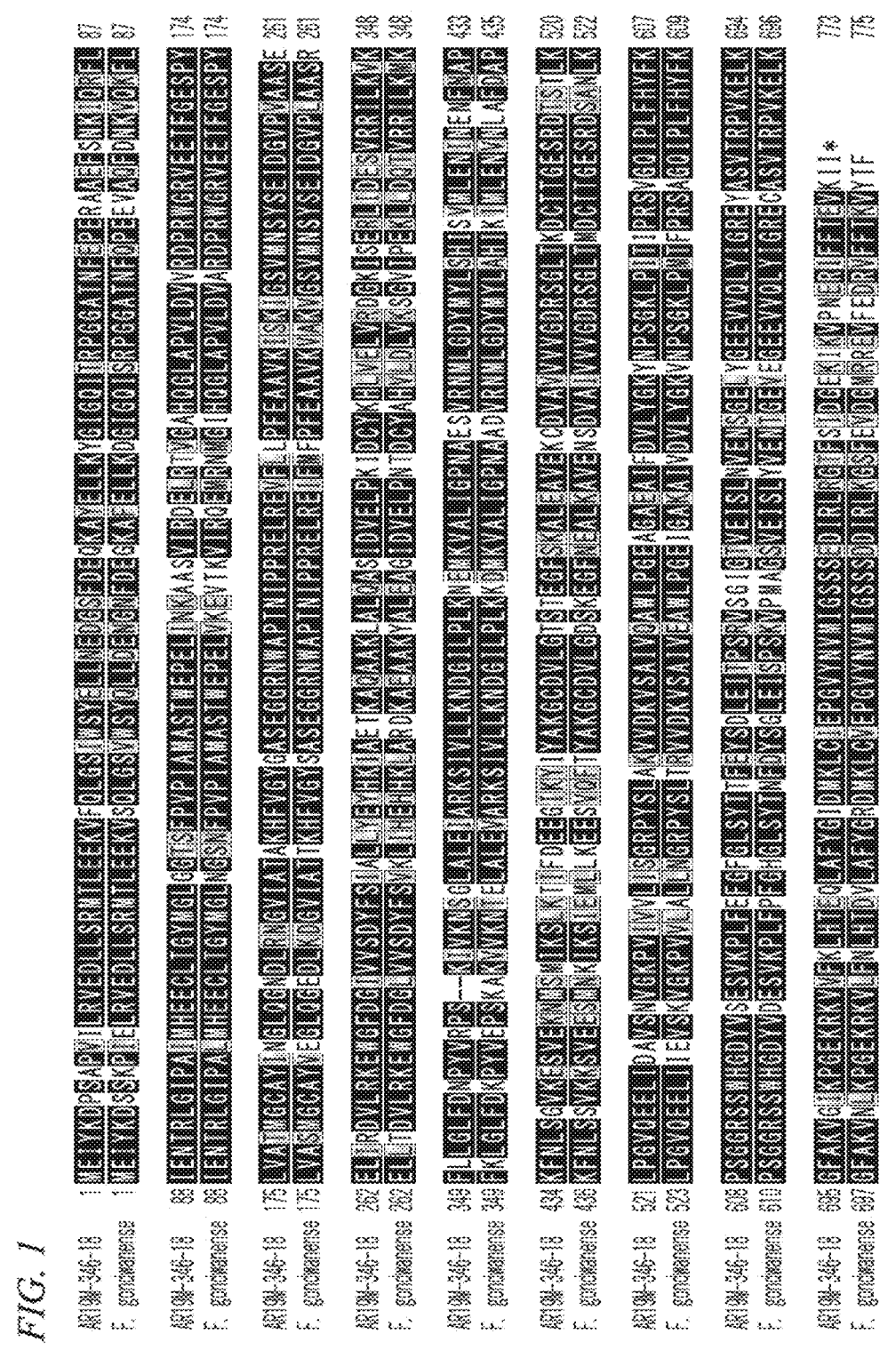

FIG. 1 shows an alignment of the amino acid sequence of the β-xylosidase catalytic domain of the gene clone AR19M-346-18 and the amino acid sequence of a GH3 xylosidase (Genbank registration ID: AFY97406.1) of a bacterium *Fervidobacterium gondwanense* belonging to the phylum Thermotogae. In FIG. 1, the black/white inverted amino acids denote the same amino acid residues (identical) throughout all of these amino acid sequences, the shaded amino acids denote similar amino acid residues (similar) in these amino acid sequences, and the symbols "-" denote deletions (gaps). The β-xylosidase catalytic domain of the gene clone AR19M-346-18 including the gaps showed 76% sequence identity with the GH3 xylosidase of *Fervidobacterium gondwanense*.

<7> Gene Expression and Purification of β-Xylosidase Enzymatic Protein

After the sequencing, the plasmids having the target gene were introduced in *E. coli* for protein expression by a heat shock method. The BL21 Star (DE3) strain furnished in the Champion pET Directional TOPO Expression Kits (manufactured by Life Technologies) was used as the competent cell for the transformation. *E. coli* having the target gene was inoculated in a LB medium containing 100 mg/L ampicillin and cultured to about OD600=0.2 to 0.8, which was then added with IPTG (isopropyl-β-D(−)-thiogalactopyranoside), and additionally cultured for 5 to 20 hours. By so doing, the expression induction of the target protein was carried out. After the culture, *E. coli* was collected by centrifugation, to which 50 mM Tris-HCl buffer (pH8.0) of ⅒-fold volume of the culture liquid was added and suspended. Thereafter, 5 minutes disrupting and 5 minutes halting processes were repeated 7 to 8 times by using an ultrasonic disruption apparatus, Astrason 3000 (manufactured by Misonix, Inc.). By so doing, the crude extract of the gene recombinant *E. coli* containing the target protein was obtained. The crude extract of the gene recombinant *E. coli* was filtrated through a filter (pore diameter φ=0.45 μm, manufactured by Millipore), and the yielded filtrate was used as a gene recombinant *E. coli* homogenate supernatant.

The gene recombinant *E. coli* homogenate supernatant was loaded onto an ion-exchange column HiTrap Q HP (manufactured by GE Healthcare) equilibrated with 50 mM Tris-HCl buffer (pH8.0), by which proteins were fractionated with 0 to 50% concentration gradient with 50 mM Tris-HCl buffer (pH8.0) containing 1M NaCl using a middle-to-high pressure liquid chromatography system AKTA design (manufactured by GE Healthcare). The fractions exhibiting β-xylosidase activity were all mixed and then subjected to solution exchange into 50 mM Tris-HCl buffer (pH8.0) containing 750 mM ammonium sulfate using a centrifugal ultrafiltration membrane VIVASPIN 20 (manufactured by Sartorius stedim). The fractions with β-xylosidase activity after the solution exchange were loaded onto a hydrophobic interaction separation column HiTrap Phnenyl HP (manufactured by GE Healthcare) equilibrated with the same solution, by which proteins were fractionated with 0 to 100% concentration gradient with 50 mM Tris-HCl buffer (pH8.0). The fractions exhibiting β-xylosidase activity were all mixed and then concentrated by using the VIVASPIN 20 until the liquid volume reached to about 8 mL. The concentrated sample was loaded onto a gel filtration column Hiload 26/60 superdex 200 pg (manufactured by GE Healthcare) equilibrated with 50 mM Tris-HCl buffer (pH8.0) containing 150 mM NaCl, and fractionated by flowing the same buffer of 1 to 1.5 fold volume of the column volume at a flow rate of 2 to 3 mL/min. The fractions exhibiting β-xylosidase activity were all mixed and then subjected to solution exchange into 1 mM phosphoric acid buffer (pH 6.8) and concentration by using the VIVASPIN 20, and then loaded onto a hydroxyapatite column CHT5-1 (manufactured by Bio-Rad Laboratories, Inc.) equilibrated with the same buffer, by which proteins were fractionated with 0 to 100% concentration gradient with 400 mM phosphoric acid buffer (pH 6.8). The fractions exhibiting β-xylosidase activity were all mixed and then subjected to solution exchange into 50 mM Tris-HCl buffer (pH8.0) and concentrated. By so doing, a purified enzyme having the final concentration of about 3.5 mg/mL was obtained.

The gene recombinant *E. coli* homogenate supernatant and the purified enzyme were checked by SDS-PAGE (SDS-polyacrylamide gel electrophoresis) analysis. 5 μg of the gene recombinant *E. coli* homogenate supernatant and 0.5 μg of the purified enzyme were respectively mixed with a four times concentrated solution of 2-mercaptoethanol containing sample buffer (manufactured by Wako Pure Chemical Industries, Ltd.) such that the buffer concentration was one times, and then treated at a temperature of 95° C. for 4 minutes, followed by electrophoresis by using a 10% Criterion TGX Stain-free Gel (Bio-Rad Laboratories, Inc.). After the completion of the electrophoresis, the protein bands were visualized by the imaging system ChemiDoc (manufactured by Bio-Rad Laboratories, Inc.).

FIG. 2 shows the SDS-PAGE analysis result of the gene recombinant *E. coli* homogenate supernatant prepared from the transformed *E. coli* introduced with the AR19M-346-18 gene and the purified enzyme which was purified from the gene recombinant *E. coli* homogenate supernatant. The lane 1 is a molecular weight marker for proteins, and the lanes 2 and 3 show the electrophoresis patterns of the gene recombinant *E. coli* homogenate supernatant or the purified enzyme, respectively. As a result, in the gene recombinant *E. coli* homogenate supernatant (lane 2), a strong band was observed near the molecular weight predicted from the amino acid sequence (SEQ ID NO: 1), and in the purified enzyme (lane 3), a single band corresponding with the above band was observed (indicated by an arrow in the figure).

<8> Measurement of β-Xylosidase Activity Using PNPX as Substrate (PNPX Hydrolysis Activity)

PNPX was used as a substrate in the measurement of the β-xylosidase activity. A solution prepared by dissolving PNPX (manufactured by Sigma-Aldrich Co. LLC.) in water and adjusting the concentration to be 3.4 mM was used as a substrate solution (hereinafter, may be referred to as a "3.4 mM PNPX aqueous solution"). It should be noted that the 3.4 mM PNPX aqueous solution prepared by the above method was used as the PNPX substrate solution used for all the following experiments.

The PNPX hydrolysis activity of the enzymatic protein (AR19M-346-18) encoded by the AR19M-346-18 gene was investigated. More specifically, a mixture solution including 100 μL of the 3.4 mM PNPX aqueous solution, 50 μL of 200 mM acetic acid buffer (pH6.0), 20 μL of either the gene recombinant *E. coli* homogenate supernatant obtained in the above-mentioned process <7> or the purified enzyme solution obtained by diluting the purified enzyme (3.5 mg/mL) to 10 ng/μL with water and 30 μL of purified water was allowed to react at a temperature of 30 to 100° C. for 20 minutes. In all the measurements, a mixture solution prepared by adding purified water instead of the gene recombinant *E. coli* homogenate supernatant or purified enzyme and reacting under the same conditions was used as the control lot. Moreover, the substrate solution and the enzyme (gene recombinant *E. coli* homogenate supernatant or purified enzyme) were respectively and separately kept at retained reaction temperatures for 5 minutes, and then mixed. This timing was set to the initiation of the reaction. During the reaction, all of the mixed solutions were set to a predetermined temperature by using the Thermomixer (manufactured by Eppendorf AG). After the completion of the reaction, the reaction was stopped by adding the same volume of a 0.2 M $Na_2CO_3$ solution to each mixture solution with stirring, followed by centrifugation. By so doing, the supernatant was obtained. The absorbance at 420 nm was measured by using a spectrophotometer, and the amount of p-nitrophenol in the supernatant was calculated by using a calibration curve prepared with p-nitrophenol. The amount of p-nitrophenol produced by the enzymatic hydrolysis was obtained by the difference from the control lot. The enzymatic activity for producing 1 μmol of p-nitrophenol per minute was defined as 1 U, and the value obtained by dividing it by the amount of protein was defined as the specific activity (U/mg). In addition, each measurement was performed by three independent experiments, from which the mean value and the standard errors were obtained.

As a result, the presence of β-xylosidase activity (PNPX hydrolysis activity) was confirmed in both cases where the gene recombinant E. coli homogenate supernatant was used and where the purified enzyme was used.

<9> Substrate Specificity of AR19M-346-18

The hydrolysis activities for various cellulose substrates and hemicellulose substrates were investigated with the enzymatic protein (AR19M-346-18) encoded by the AR19M-346-18 gene. In the measurement, a purified enzyme solution prepared by diluting the purified enzyme (concentration of 3.5 mg/mL) obtained from the above-mentioned process <7> to 10 ng/μL with water was used. In addition, as substrates, PNPX (manufactured by Sigma-Aldrich Co. LLC.), PNPG (manufactured by Sigma-Aldrich Co. LLC.), PSA, an Avicel powder, CMC (manufactured by Sigma-Aldrich Co. LLC.), xylan (derived from beechwood, manufactured by Sigma-Aldrich Co. LLC.), lichenan (manufactured by MP Biomedicals, LLC.), and laminarin (derived from *Laminaria digitata*, manufactured by Sigma-Aldrich Co. LLC.) were used.

PSA was prepared by once dissolving an Avicel powder (fine crystalline cellulose powder, manufactured by Merck) with a phosphoric acid solution, then precipitating it by adding sterile purified water, and thereafter washing the same until the pH reached 5 or higher. It should be noted that PSA used for all the following experiments was prepared by the above method.

More specifically, the enzymatic reaction was carried out by first preincubating a mixture solution composed of 50 μL of 200 mM acetic acid buffer (pH6.0), 20 μL of the purified enzyme solution (10 ng/μL) and 30 μL of purified water as a reaction solution at a temperature of 70° C. for 5 minutes, then additionally adding 100 μL of each substrate solution (1% by mass aqueous solutions of PSA, Avicel powder, CMC, xylan, lichenan and laminarin, and 3.4 mM aqueous solutions of PNPG and PNPG) thereto, and incubating the resulting mixture solution at a temperature of 70° C. for 20 minutes (2 hours when the Avicel powder was used as a substrate). When PSA, Avicel powder, or xylan was used as a substrate, during the reaction, the mixture solution was stirred by applying vibration of 1,400 rpm using the Thermomixer (manufactured by Eppendorf AG) so as to avoid the precipitation of insoluble substrates.

After the completion of the reaction, in the reaction where PNPG or PNPX was used as the substrate, as in the case of investigating the PNPX hydrolysis activity of AR19M-346-18 of the above-mentioned process <8>, the absorbance at 420 nm of the supernatant of the mixture solution after the reaction was measured, the amount of p-nitrophenol produced by the hydrolysis was obtained, and the specific activity (U/mg) was calculated. After the completion of the reaction, in the reaction where PSA, Avicel powder, CMC, xylan, lichenan or laminarin was used as a substrate, the same volume of a 3,5-dinitrosalicylic acid reagent (DNS solution) was added. The resulting mixture was treated by heating at a temperature of 100° C. for 5 minutes, cooled down on ice for 5 minutes, and then centrifuged at 25° C., and 15,000 g for 5 minutes. By so doing, the supernatant was obtained. The absorbance at 540 nm was measured by using a spectrophotometer, and the amount of reduced sugar in the supernatant was calculated by using a calibration curve prepared with glucose (calibration curve prepared with xylose when xylan was used as a substrate). The amount of reduced sugar produced by the enzymatic hydrolysis was obtained by the difference from the control lot. The enzymatic activity for producing 1 μmol of reduced sugar per minute was defined as 1 U, and the value obtained by dividing it by the amount of protein was defined as the specific activity (U/mg).

Figure 3:
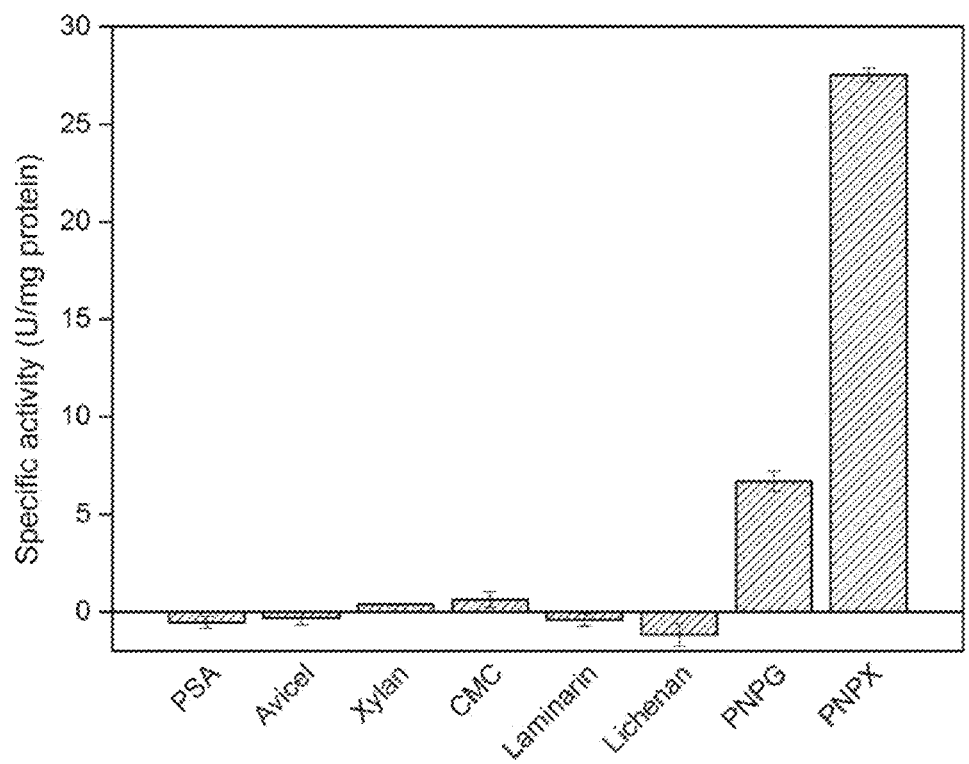
FIG. 3 is a diagram showing the measurement results of the hydrolytic activity of the AR19M-346-18 protein expressed in *E. coli* in Example 1 for each substrate.

Each measurement was performed by three independent experiments, from which the mean value and the standard errors were obtained. The measurement results are shown in FIG. 3. As a result, AR19M-346-18 exhibited high hydrolysis activity for PNPX, and also exhibited degradation activity for PNPG. On the other hand, it exhibited almost no degradation activity for other substrates.

<10> pH and Temperature Dependencies of β-Xylosidase Activity Using PNPX as Substrate The temperature dependency and the pH dependency of the PNPX hydrolysis activity of the enzymatic protein (AR19M-346-18) encoded by the AR19M-346-18 gene were investigated. In the measurement, a purified enzyme solution prepared by diluting the purified enzyme (concentration of 3.5 mg/mL) obtained from the above-mentioned process <7> to 10 ng/μL with water was used.

The measurement of the pH dependency of the PNPX hydrolysis activity of the purified AR19M-346-18 was conducted in the same manner as that of the above-mentioned process <8>, except for reacting a mixture solution composed of 100 μL of the 3.4 mM PNPX aqueous solution, and 50 μL of McIlvaine buffer (pH3 to 8), 50 μL of acetic acid buffer (pH3.5 to 6), or 50 μL of phosphoric acid buffer (pH6 to 8), 30 μL of purified water and 20 μL of the purified enzyme solution (10 ng/μL), at a temperature of 70° C. for 20 minutes, wherein the amount of p-nitrophenol produced by the enzymatic hydrolysis was obtained, and the PNPX hydrolysis activity (U/mg) was calculated.

The measurement of the temperature dependency of the PNPX hydrolysis activity of the purified AR19M-346-18 was conducted in the same manner as that of the above-mentioned process <8>, except that the reaction was carried out at a reaction temperature of 30, 40, 50, 60, 65, 70, 75, 80, 85, 90, 95, or 100° C., wherein the amount of p-nitrophenol produced by the enzymatic hydrolysis was obtained, and the PNPX hydrolysis activity (U/mg) was calculated.

Figure 4:
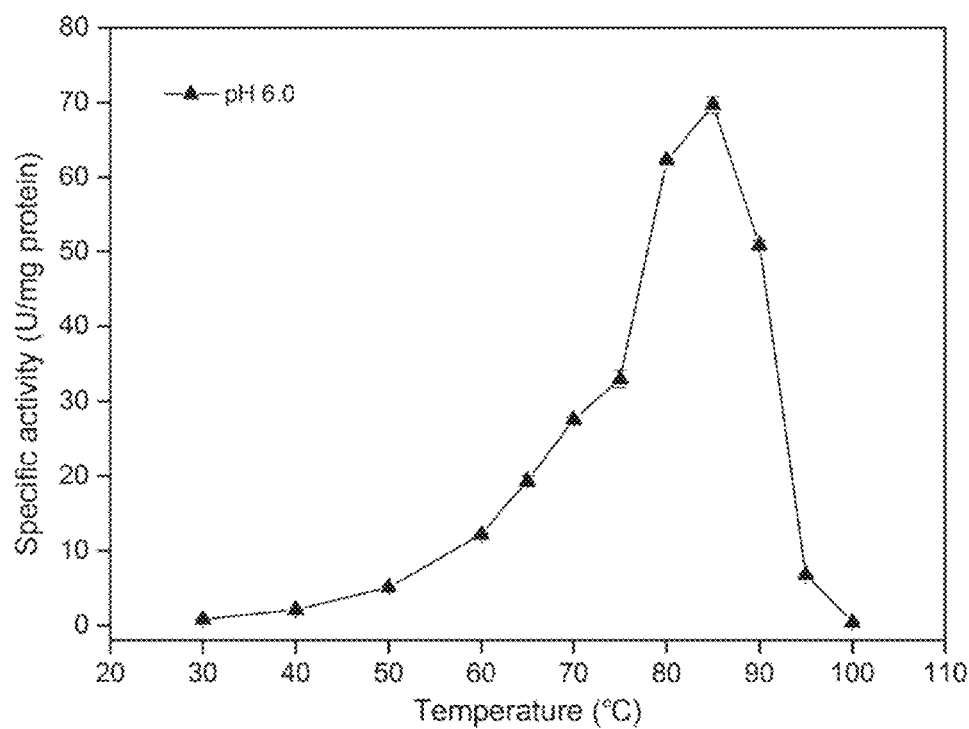
FIG. 4 is a diagram showing the results of the PNPX hydrolysis activity (pH 6.0) of the AR19M-346-18 protein expressed in *E. coli* measured at respective temperatures in Example 1.
Figure 5:
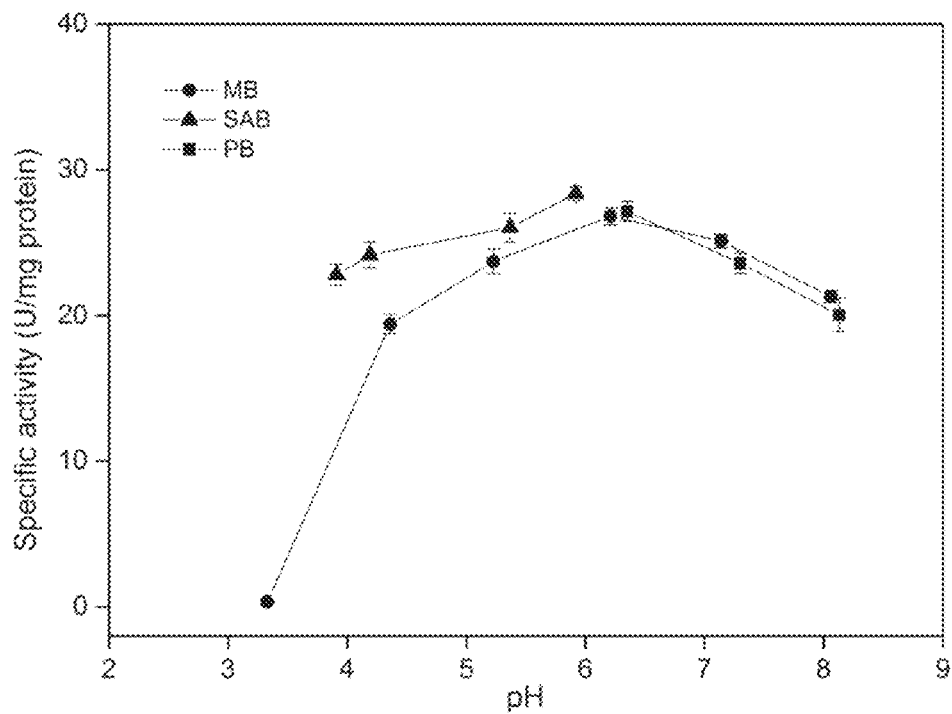
FIG. 5 is a diagram showing the results of the PNPX hydrolysis activity (70° C.) of the AR19M-346-18 protein expressed in *E. coli* measured at respective pH values in Example 1.

The measurement results are shown in FIGS. 4 and 5. FIG. 4 is a diagram showing the measurement results of the PNPX hydrolysis activity (pH6.0) of the purified enzyme AR19M-346-18 at respective temperatures, wherein the horizontal axis represents the temperature. FIG. 5 is a diagram showing the measurement results of the PNPX hydrolysis activity (70° C.) of the purified enzyme AR19M-346-18 at respective pH values, wherein the horizontal axis represents the pH. In FIG. 5, "MB" shows the results when the McIlvaine buffer (pH3 to 8) was used, "SAB" shows the results when the acetic acid buffer (pH3.5 to 6) was used, and "PB" shows the results when the phosphoric acid buffer (pH6 to 8) was used, respectively. The pH was plotted by the actual measurement values of the mixture solution containing the substrate, the buffer, and the enzyme.

The purified enzyme of AR19M-346-18 exhibited high PNPX hydrolysis activity in a temperature range from 80 to 90° C. (FIG. 4). The optimum temperature ($T_{opt}$) showing the highest activity was 85° C. at a pH of 6.0. When the enzymatic reaction temperature was set to 95° C. or higher, the PNPX hydrolysis activity of the purified enzyme of AR19M-346-18 was rapidly decreased.

In addition, the purified enzyme of AR19M-346-18 exhibited PNPX hydrolysis activity within a range of pH4.0 to 8.0 at the reaction temperature of 70° C. In particular, the purified enzyme of AR19M-346-18 exhibited the highest PNPX hydrolysis activity at a reaction temperature of 70° C. and a pH of 6.

<11> Thermal Stability Measurement of β-Xylosidase by Differential Scanning Fluorimetry Differential scanning fluorimetry (DSF) is one of the methods of measuring the thermal denaturation of proteins using a fluorescent dye and real-time PCR machine, and can be applied to various proteins. The fluorescent dyes used in DSF such as SYPRO Orange emit fluorescence in the nonpolar conditions when binding to the hydrophobic site, while the emission is suppressed in the polar conditions when dissolved in water. Usually, the protein structure is unfolded in the thermal denaturation temperature, and the internal hydrophobic sites of the protein are exposed to the protein surface. When SYPRO Orange binds to these exposed hydrophobic sites, by the excitation light having a wavelength of 470 to 480 nm, strong fluorescence having a peak near a wavelength of 595 nm is emitted. By increasing the temperature of the protein solution at regular intervals in a stepwise manner and measuring the fluorescence intensity, the thermal degradation temperature (=change point of the fluorescence intensity) is calculated.

In the measurement, a purified enzyme solution prepared by adjusting the purified enzyme (3.5 mg/mL) obtained from the above-mentioned process <7> to 1 mg/mL with water was used.

More specifically, 2 μL of 100-fold diluted SYPRO Orange (manufactured by Life Technologies), 1 μL of the purified enzyme solution with a concentration of 1 mg/mL, 5 μL of 200 mM phosphoric acid buffer (pH 6.0) and 12 μL of purified water were added into the wells of a 96-well PCR plate (Multiplate 96 Well PCR Plate MLL-9651, manufactured by Bio-Rad Laboratories, Inc.) so that the volume of each well was 20 μL. The PCR plate was sealed with Optical Flat 8-Cap Strips (manufactured by Bio-Rad Laboratories, Inc.), the temperature of the well was increased by 0.2° C. from 30° C. up to 100° C. by a real-time PCR machine (CFX96 Touch Real-Time PCR System, manufactured by Bio-Rad Laboratories, Inc.), and following a lapse of 10 seconds after the target temperature was achieved, the fluorescence intensity of each well was measured simultaneously. SYPRO Orange was excited by a light emitting diode (LED) having a wavelength range of 450 to 490 nm, the SYPRO Orange emitted light was passed through a band pass filter of 560 to 580 nm range, the measurement of the fluorescence intensity was performed with a CCD camera, and changes in the fluorescence intensity were plotted as a function of temperature. The data analysis was carried out using the analysis software CFX Manager (manufactured by Bio-Rad Laboratories, Inc.) supplied with the real-time PCR machine.

Figure 6:
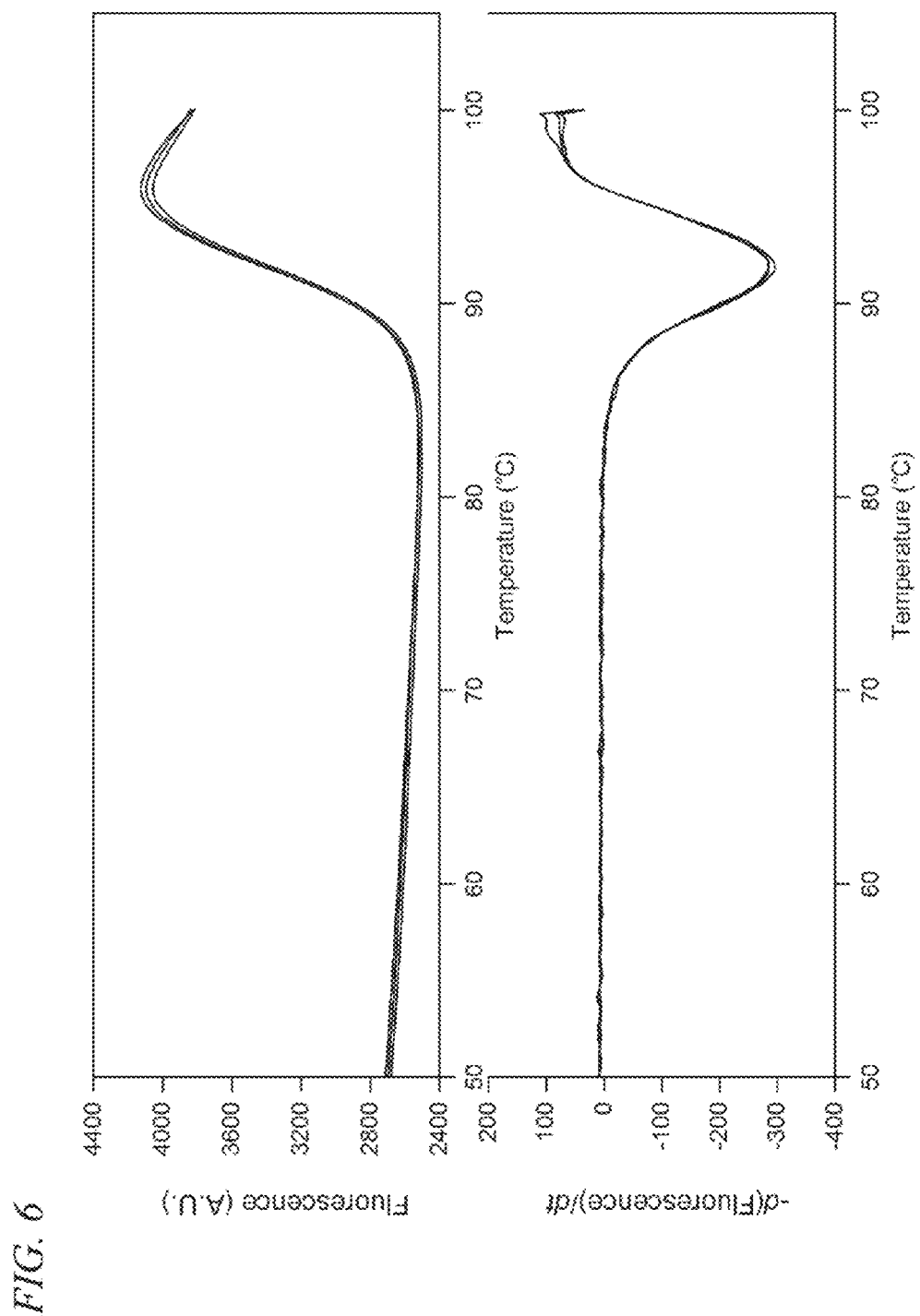
FIG. 6 is a diagram showing a change in the fluorescence intensity of SYPRO Orange caused in association with the thermal denaturation exhibited by the AR19M-346-18 protein expressed in *E. coli* in Example 1.

FIG. 6 shows changes in the fluorescence intensity of SYPRO Orange caused in association with the thermal denaturation exhibited by the AR19M-346-18 enzymatic protein which was measured by the DSF method. The upper graph in FIG. 6 shows measured data, and the lower graph in FIG. 6 shows the first derivative "−d(Fluorescence)/dt" of the fluorescence intensity change curve in the upper graph of FIG. 6. The thermal denaturation temperature (melting temperature; Tm value) was defined as the local maximum value of the first derivative ("−d(Fluorescence)/dt" shown on the Y axis of the lower graph in FIG. 6) of the fluorescence intensity curve that is a function of temperature. The thermal denaturation temperature (Tm) of the AR19M-346-18 enzymatic protein obtained from the first derivative of the fluorescence intensity curve was 91.9±0.1° C. (n=3) when the pH was 6.0, showing a value close to the optimum temperature $T_{opt}$=85° C. obtained by the PNPX hydrolysis activity.

[Sequence Listing]

What is claimed is:

1. A thermostable β-xylosidase comprising
an isolated polypeptide consisting of the amino acid sequence of SEQ ID NO: 1 and
at least one region selected from the group consisting of a Fibronectin type III-like domain, a linker domain, a signal peptide and a tag.

* * * * *

SEQUENCE LISTING

```
<160> NUMBER OF SEQ ID NOS: 7

<210> SEQ ID NO 1
<211> LENGTH: 773
<212> TYPE: PRT
<213> ORGANISM: Unknown
<220> FEATURE:
<223> OTHER INFORMATION: AR19M-346-18

<400> SEQUENCE: 1

Met Glu Ile Tyr Lys Asp Pro Ser Ala Pro Val Ile Leu Arg Val Glu
  1               5                  10                  15

Asp Leu Leu Ser Arg Met Thr Leu Glu Glu Lys Val Phe Gln Leu Gly
                 20                  25                  30

Ser Ile Trp Ser Tyr Glu Leu Leu Asn Glu Asp Gly Ser Phe Asp Glu
             35                  40                  45

Gln Lys Ala Tyr Glu Leu Leu Lys Tyr Gly Ile Gly Gln Ile Thr Arg
         50                  55                  60

Pro Gly Gly Ala Thr Asn Phe Glu Pro Glu Arg Ala Ala Glu Phe Ser
 65                  70                  75                  80

Asn Lys Ile Gln Arg Phe Leu Ile Glu Asn Thr Arg Leu Gly Ile Pro
                 85                  90                  95
```

```
Ala Ile Met His Glu Glu Cys Leu Thr Gly Tyr Met Gly Leu Gly Gly
            100                 105                 110

Thr Ser Phe Pro Val Pro Ile Ala Met Ala Ser Thr Trp Glu Pro Glu
            115                 120                 125

Leu Ile Asn Lys Ala Ala Ser Val Ile Arg Asp Glu Leu Arg Thr Val
            130                 135                 140

Gly Ala His Gln Gly Leu Ala Pro Val Leu Asp Val Val Arg Asp Pro
145                 150                 155                 160

Arg Trp Gly Arg Val Glu Glu Thr Phe Gly Glu Ser Pro Tyr Leu Val
                165                 170                 175

Ala Thr Met Gly Cys Ala Tyr Ile Asn Gly Leu Gln Gly Asn Asp Leu
            180                 185                 190

Arg Asn Gly Val Ile Ala Thr Ala Lys His Phe Val Gly Tyr Gly Ala
            195                 200                 205

Ser Glu Gly Gly Arg Asn Trp Ala Pro Thr Asn Ile Pro Pro Arg Glu
210                 215                 220

Leu Arg Glu Val Phe Leu Leu Pro Phe Glu Ala Ala Val Lys Ile Ser
225                 230                 235                 240

Lys Ile Gly Ser Val Met Asn Ser Tyr Ser Glu Ile Asp Gly Val Pro
                245                 250                 255

Val Ala Ala Ser Glu Glu Leu Ile Arg Asp Val Leu Arg Lys Glu Trp
            260                 265                 270

Gly Phe Asp Gly Ile Val Val Ser Asp Tyr Phe Ser Ile Ala Leu Leu
            275                 280                 285

Tyr Glu Tyr His Lys Ile Ala Glu Thr Lys Ala Gln Ala Ala Lys Leu
            290                 295                 300

Ala Leu Gln Ala Ser Ile Asp Val Glu Leu Pro Lys Ile Asp Cys Tyr
305                 310                 315                 320

Lys His Leu Val Glu Leu Val Arg Asp Gly Lys Ile Ser Glu Arg Leu
                325                 330                 335

Ile Asp Glu Ser Val Arg Arg Ile Leu Lys Val Lys Phe Leu Leu Gly
            340                 345                 350

Leu Phe Asp Asn Pro Tyr Val Arg Pro Ser Lys Ile Val Lys Asn Ser
            355                 360                 365

Gly Leu Ala Leu Glu Ile Ala Arg Lys Ser Ile Val Leu Leu Lys Asn
370                 375                 380

Asp Gly Ile Leu Pro Leu Lys Asn Glu Met Lys Val Ala Leu Ile Gly
385                 390                 395                 400

Pro Asn Ala Glu Ser Val Arg Asn Met Leu Gly Asp Tyr Met Tyr Leu
                405                 410                 415

Ser His Ile Ser Val Met Leu Glu Asn Ile Asn Glu Asn Phe Asn Ala
            420                 425                 430

Pro Lys Phe Asn Leu Ser Gly Val Lys Glu Ser Val Glu Lys Asn Met
            435                 440                 445

Ser Met Ile Lys Ser Leu Lys Thr Ile Phe Asp Glu Glu Gly Ile Lys
            450                 455                 460

Tyr Ile Tyr Ala Lys Gly Cys Asp Val Leu Gly Thr Ser Thr Glu Gly
465                 470                 475                 480

Phe Ser Lys Ala Leu Glu Ala Val Glu Lys Cys Asp Val Ala Val Val
                485                 490                 495

Val Val Gly Asp Arg Ser Gly Leu Thr Lys Asp Cys Thr Thr Gly Glu
            500                 505                 510
```

| | | | | | | | | | | | |
|---|---|---|---|---|---|---|---|---|---|---|---|
|Ser|Arg|Asp|Thr|Ser|Thr|Leu|Lys|Leu|Pro|Gly|Val|Gln|Glu|Leu|
| |515| | | |520| | | |525| | | | | |

Ser Arg Asp Thr Ser Thr Leu Lys Leu Pro Gly Val Gln Glu Leu
            515                 520                 525

Ile Asp Ala Val Ser Asn Val Gly Lys Pro Val Ile Val Leu Ile
    530                 535                 540

Ser Gly Arg Pro Tyr Ser Leu Ala Lys Val Val Asp Lys Val Ser Ala
545                 550                 555                 560

Ile Val Gln Ala Trp Leu Pro Gly Glu Ala Gly Ala Glu Ala Ile Phe
                565                 570                 575

Asp Val Leu Tyr Gly Lys Tyr Asn Pro Ser Gly Lys Leu Pro Ile Thr
            580                 585                 590

Ile Pro Arg Ser Val Gly Gln Ile Pro Leu Phe His Tyr Phe Lys Pro
        595                 600                 605

Ser Gly Gly Arg Ser Ser Trp His Gly Asp Tyr Val Ser Glu Ser Val
    610                 615                 620

Lys Pro Leu Phe Glu Phe Gly Phe Gly Leu Ser Tyr Thr Thr Phe Glu
625                 630                 635                 640

Tyr Ser Asp Leu Glu Ile Thr Pro Ser Arg Val Ser Gly Ile Gly Thr
                645                 650                 655

Val Glu Ile Ser Leu Asn Val Glu Asn Ser Gly Glu Leu Tyr Gly Glu
            660                 665                 670

Glu Val Val Gln Leu Tyr Ile Gly Arg Glu Tyr Ala Ser Val Thr Arg
        675                 680                 685

Pro Val Lys Glu Leu Lys Gly Phe Ala Lys Val Gly Ile Lys Pro Gly
    690                 695                 700

Glu Lys Arg Lys Val Val Phe Lys Leu His Thr Glu Gln Leu Ala Phe
705                 710                 715                 720

Tyr Gly Ile Asp Met Lys Leu Cys Ile Glu Pro Gly Val Tyr Asn Val
                725                 730                 735

Met Ile Gly Ser Ser Ser Glu Asp Ile Arg Leu Arg Gly Thr Phe Ser
            740                 745                 750

Ile Asp Gly Glu Lys Ile Lys Val Pro Asn Glu Arg Ile Phe Phe Thr
        755                 760                 765

Glu Val Lys Ile Ile
    770

<210> SEQ ID NO 2
<211> LENGTH: 2322
<212> TYPE: DNA
<213> ORGANISM: Unknown
<220> FEATURE:
<223> OTHER INFORMATION: Open reading frame AR19M-346

<400> SEQUENCE: 2

```
atggagattt ataaggatcc aagcgcgcca gtgattttgc gagttgaaga tttgctttct    60
agaatgactt tggaagaaaa agttttcag ttgggttcaa tttggagcta tgaactactg    120
aatgaagatg aagtttcga cgagcaaaaa gcatatgagc ttttgaaata cggcataggt    180
caaattacta ggccaggcgg tgctacaaat ttcgaacctg aacgcgctgc agaatttagc    240
aataaaatcc agaggtttct cattgaaaac acaagacttg aatacctgc tataatgcac    300 gaagaatgct tgactgggta catgggactt ggtggtacaa gttttccggt accaattgct    360
atggcaagta cttgggaacc agaactgatt aacaaggctg cgtctgtcat tcgagatgaa    420
ctcagaacag ttggtgctca ccaaggcctt gcaccggtac ttgatgttgt tcgggatccc    480
agatggggaa gggtagaaga aacttttgga gagtctccgt atcttgtggc aacgatggga    540
```

| | |
|---|---|
| tgcgcttata tcaacggcct acaaggaaat gacctaagaa acggagttat tgcaactgct | 600 |
| aaacattttg ttggttacgg agcatccgaa ggcggaagga actgggcacc gacgaatata | 660 |
| ccacctcgtg aattaagaga ggtgtttctc ttaccgtttg aggccgctgt gaagatttca | 720 |
| aaaatcggtt cagtgatgaa ttcgtacagt gaaatcgacg gagtcccagt agctgcttct | 780 |
| gaggaactca tccgcgatgt gcttagaaag gaatgggggt ttgatggtat agttgtttcc | 840 |
| gattattttt ccatagcact tttgtatgag tatcataaaa ttgctgagac caaagcacaa | 900 |
| gcagccaagc tcgcgcttca agcctctatc gatgttgaat acccaagat tgactgttac | 960 |
| aagcatctcg tagagttggt gagggatggc aaaatttcgg aaaggctgat agatgaatcg | 1020 |
| gtgagaagga tcctaaaggt taagttcctg cttggattat ttgataatcc ttacgttcga | 1080 |
| ccgtcgaaga tcgttaagaa ttctggacta gctctcgaaa tcgctagaaa atctatagtt | 1140 |
| ctgcttaaaa acgatggtat tcttccgcta aaaaacgaaa tgaaagttgc gctgatagga | 1200 |
| cctaatgcgg aaagtgttag aaatatgtta ggcgattata tgtacctttc tcacatcagt | 1260 |
| gtgatgcttg aaaatataaa tgagaatttc aatgctccga aattcaatct ctctggtgtt | 1320 |
| aaagaatcgg tagagaaaaa tatgagtatg attaagagtt tgaaaactat attcgatgaa | 1380 |
| gagggcataa aatacatcta cgctaagggt tgcgatgttc tgggaacgtc taccgaagga | 1440 |
| ttcagcaaag cattagaagc ggttgaaaaa tgtgacgtcg cagttgttgt ggtcggtgac | 1500 |
| aggtcaggtt tgacaaaaga ttgcactaca ggggagtcaa gggatacatc tactttaaaa | 1560 |
| ctacccggtg ttcaggaaga gttgattgac gcagtttcaa atgtgggtaa gcctgtgata | 1620 |
| gttgttttga taagtggcag accatattct cttgctaaag ttgtcgataa agtgtcggct | 1680 |
| atagttcagg catggttacc tggagaagcg ggagcagaag cgatatttga tgttctgtat | 1740 |
| gggaagtata atccatctgg aaagcttcct ataacaattc cgagaagtgt tggacagatt | 1800 |
| ccgctcttcc attattttaa accatctggt ggcagatcaa gctggcatgg tgattatgtt | 1860 |
| tccgagagtg tcaaaccact tttttgagttt ggttttggac tatcgtacac aacctttgag | 1920 |
| tacagcgatt tagaaatcac accatcgaga gtaagtggta tcgggacagt tgaaatttct | 1980 |
| ttaaatgtcg agaacagcgg agagctgtac ggtgaggaag ttgttcaact ctacatagga | 2040 |
| agagaatacg cttcagtcac acgccctgtg aaagagttaa agggatttgc aaaagttggt | 2100 |
| ataaaaccgg gagaaaagag gaaggttgtt ttcaaattgc acacagaaca gttggcgttt | 2160 |
| tatggaatag atatgaagct atgtatcgaa ccaggtgtgt acaatgtcat gattggtagt | 2220 |
| tcgtctgaag atatacgact ccgtggaacg ttttcaatag atggtgagaa aataaaagtt | 2280 |
| ccaaatgaaa ggatattctt taccgaggtt aaaattatat aa | 2322 |

<210> SEQ ID NO 3
<211> LENGTH: 2322
<212> TYPE: DNA
<213> ORGANISM: Unknown
<220> FEATURE:
<223> OTHER INFORMATION: Gene AR19M-346-18

<400> SEQUENCE: 3

| | |
|---|---|
| atggagattt ataaggatcc aagcgcgcca gtgattttgc gagttgaaga tttgctttct | 60 |
| agaatgactt tggaagaaaa agtttttcag ttgggttcaa tttggagcta tgaactactg | 120 |
| aatgaagatg gaagtttcga cgagcaaaaa gcatatgagc ttttgaaata cggcataggt | 180 |
| caaattacta ggccaggcgg tgctacaaat ttcgaacctg aacgcgctgc agaatttagc | 240 |
| aataaaaatcc agaggtttct cattgaaaac acaagacttg gaatacctgc tataatgcac | 300 |

```
gaagaatgct tgactgggta catgggactt ggtggtacaa gttttccggt accaattgct    360
atggcaagta cttgggaacc agaactgatt aacaaggctg cgtctgtcat tcgagatgaa    420
ctcagaacag ttggtgctca ccaaggcctt gcaccggtac ttgatgttgt tcgggatccc    480
agatggggaa gggtagaaga aacttttgga gagtctccgt atcttgtggc aacgatggga    540
tgcgcttata tcaacggcct acaaggaaat gacctaagaa acggagttat tgcaactgct    600
aaacattttg ttggttacgg agcatccgaa ggcggaagga actgggcacc gacgaatata    660
ccacctcgtg aattaagaga ggtgtttctc ttaccgtttg aggccgctgt gaagatttca    720
aaaatcggtt cagtgatgaa ttcgtacagt gaaatcgacg gagtcccagt agctgcttct    780
gaggaactca tccgcgatgt gcttagaaag gaatgggggt ttgatggtat agttgtttcc    840
gattattttt ccatagcact tttgtatgag tatcataaaa ttgctgagac caaagcacaa    900
gcagccaagc tcgcgcttca agcctctatc gatgttgaat acccaagat tgactgttac    960 aagcatctcg tagagttggt gagggatggc aaaatttcgg aaaggctgat agatgaatcg    1020
gtgagaagga tcctaaaggt taagttcctg cttggattat ttgataatcc ttacgttcga    1080
ccgtcgaaga tcgttaagaa ttctggacta gctctcgaaa tcgctagaaa atctatagtt    1140
ctgcttaaaa acgatggtat tcttccgcta aaaaacgaaa tgaaagttgc gctgatagga    1200
cctaatgcgg aaagtgttag aaatatgtta ggcgattata tgtaccttc tcacatcagt    1260 gtgatgcttg aaaatataaa tgagaatttc aatgctccga aattcaatct ctctggtgtt    1320
aaagaatcgg tagagaaaaa tatgagtatg attaagagtt tgaaaactat attcgatgaa    1380
gagggcataa aatacatcta cgctaagggt tgcgatgttc tgggaacgtc taccgaagga    1440
ttcagcaaag cattagaagc ggttgaaaaa tgtgacgtcg cagttgttgt ggtcggtgac    1500
aggtcaggtt tgacaaaaga ttgcactaca ggggagtcaa gggatacatc tacttaaaa    1560 ctacccggtg ttcaggaaga gttgattgac gcagtttcaa atgtgggtaa gcctgtgata    1620
gttgttttga taagtggcag accatattct ctcgctaaag ttgtcgataa agtgtcggct    1680
atagttcagg catggttacc tggagaagcg ggagcagaag cgatatttga tgttctgtat    1740
gggaagtata atccatctgg aaagcttcct ataacaattc cgagaagtgt tggacagatt    1800
ccgctcttcc attatttaa accatctggt ggcagatcaa gctggcatgg tgattatgtt    1860
tccgagagtg tcaaaccact ttttgagttt ggttttggac tatcgtacac aacctttgag    1920
tacagcgatt tagaaatcac accatcgaga gtaagtggta tcgggacagt tgaaatttct    1980
ttaaatgtcg agaacagcgg agagctgtac ggtgaggaag ttgttcaact ctacatagga    2040
agagaatacg cttcagtcac acgccctgtg aaagagttaa agggatttgc aaaagttggt    2100
ataaaaccgg gagaaaagag gaaggttgtt ttcaaattgc acacagaaca gttggcgttt    2160
tatggaatag atatgaagct atgtatcgaa ccaggtgtgt acaatgtcat gattggtagt    2220
tcgtctgaag atatacgact ccgtggaacg ttttcaatag atggtgagaa aataaaagtt    2280
ccaaatgaaa ggatattctt taccgaggtt aaaattatat aa                      2322
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer.

<400> SEQUENCE: 4

```
atggagattt ataaggatcc a                                               21
```

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer.

<400> SEQUENCE: 5

```
ttatataatt ttaacctcgg taaagaatat cctttt                               35
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer.

<400> SEQUENCE: 6

```
caccatggag atttataagg atcca                                           25
```

<210> SEQ ID NO 7
<211> LENGTH: 775
<212> TYPE: PRT
<213> ORGANISM: Fervidobacterium gondwanense
<220> FEATURE:
<223> OTHER INFORMATION: GH3 xylosidase

<400> SEQUENCE: 7

Met Glu Ile Tyr Lys Asp Ser Ser Lys Pro Ile Glu Leu Arg Val Glu
 1               5                  10                  15

Asp Leu Leu Ser Arg Met Thr Leu Glu Glu Lys Val Ser Gln Leu Gly
            20                  25                  30

Ser Val Trp Ser Tyr Gln Leu Leu Asp Glu Asn Gly Asn Phe Asp Glu
        35                  40                  45

Gly Lys Ala Phe Glu Leu Leu Lys Asp Gly Ile Gly Gln Ile Ser Arg
    50                  55                  60

Pro Gly Gly Ala Thr Asn Phe Gln Pro Glu Glu Val Ala Gln Phe Asp
65                  70                  75                  80

Asn Lys Val Gln Lys Phe Leu Ile Glu Asn Thr Arg Leu Gly Ile Pro
                85                  90                  95

Ala Leu Met His Glu Glu Cys Leu Thr Gly Tyr Met Gly Leu Asn Gly
            100                 105                 110

Ser Asn Phe Pro Val Pro Ile Ala Met Ala Ser Thr Trp Glu Pro Glu
        115                 120                 125

Leu Val Lys Glu Val Thr Lys Val Ile Arg Gln Glu Met Arg Asn Met
    130                 135                 140

Gly Ile His Gln Gly Leu Ala Pro Val Leu Asp Val Ala Arg Asp Pro
145                 150                 155                 160

Arg Trp Gly Arg Val Glu Glu Thr Phe Gly Glu Ser Pro Tyr Leu Val
                165                 170                 175

Ala Ser Met Gly Cys Ala Tyr Val Glu Gly Leu Gln Gly Glu Asp Leu
            180                 185                 190

Lys Asp Gly Val Ile Ala Thr Lys His Phe Val Gly Tyr Ser Ala
        195                 200                 205

Ser Glu Gly Gly Arg Asn Trp Ala Pro Thr Asn Ile Pro Pro Arg Glu
    210                 215                 220

Leu Arg Glu Ile Phe Met Phe Pro Phe Glu Ala Ala Val Lys Val Ala

```
              225                 230                 235                 240
Lys Val Gly Ser Val Met Asn Ser Tyr Ser Glu Ile Asp Gly Val Pro
                245                 250                 255
Leu Ala Ala Ser Arg Glu Leu Leu Thr Asp Val Leu Arg Lys Glu Trp
                260                 265                 270
Gly Phe Asp Gly Leu Val Val Ser Asp Tyr Phe Ser Val Lys Leu Ile
                275                 280                 285
His Glu His His Lys Leu Ala Arg Asp Lys Ala Glu Ala Ala Lys Tyr
                290                 295                 300
Ala Leu Glu Ala Gly Ile Asp Val Glu Leu Pro Asn Thr Asp Cys Tyr
305                 310                 315                 320
Ala His Val Leu Asp Leu Val Lys Ser Gly Val Ile Pro Glu Lys Leu
                325                 330                 335
Leu Asp Gln Thr Val Arg Arg Ile Leu Lys Met Lys Phe Lys Leu Gly
                340                 345                 350
Leu Phe Asp Lys Pro Tyr Val Glu Pro Ser Lys Ala Lys Val Val Lys
                355                 360                 365
Asn Thr Glu Leu Ala Leu Glu Val Ala Arg Lys Ser Ile Val Leu Leu
370                 375                 380
Lys Asn Asp Gly Ile Leu Pro Leu Lys Lys Asp Met Lys Val Ala Leu
385                 390                 395                 400
Ile Gly Pro Asn Ala Ala Asp Val Arg Asn Met Leu Gly Asp Tyr Met
                405                 410                 415
Tyr Leu Ala His Ile Lys Ile Met Leu Glu Asn Val Asn Leu Ala Phe
                420                 425                 430
Asp Ala Pro Lys Phe Asn Leu Ser Ser Val Lys Lys Ser Val Glu Glu
                435                 440                 445
Ser Met Asn Lys Ile Lys Ser Ile Glu Met Leu Leu Lys Glu Glu Ser
                450                 455                 460
Val Gln Phe Thr Tyr Ala Lys Gly Cys Asp Val Leu Gly Asp Ser Lys
465                 470                 475                 480
Glu Gly Phe Asn Glu Ala Leu Lys Ala Val Glu Asn Ser Asp Val Ala
                485                 490                 495
Ile Val Val Val Gly Asp Arg Ser Gly Leu Thr Met Asp Cys Thr Thr
                500                 505                 510
Gly Glu Ser Arg Asp Ser Ala Asn Leu Lys Leu Pro Gly Val Gln Glu
                515                 520                 525
Glu Leu Ile Ile Glu Val Ser Lys Val Gly Lys Pro Val Val Leu Ala
                530                 535                 540
Leu Leu Asn Gly Arg Pro Tyr Ser Leu Thr Arg Val Val Asp Lys Val
545                 550                 555                 560
Ser Ala Ile Val Glu Ala Trp Leu Pro Gly Ile Gly Ala Lys Ala
                565                 570                 575
Ile Val Asp Val Leu Tyr Gly Lys Val Asn Pro Ser Gly Lys Leu Pro
                580                 585                 590
Met Thr Phe Pro Arg Ser Ala Gly Gln Ile Pro Leu Phe His Tyr Phe
                595                 600                 605
Lys Pro Ser Gly Gly Arg Ser Ser Trp His Gly Asp Tyr Val Asp Glu
                610                 615                 620
Ser Val Lys Pro Leu Phe Pro Phe Gly His Gly Leu Ser Tyr Thr Asn
625                 630                 635                 640
Phe Asp Tyr Ser Gly Leu Glu Ile Ser Pro Ser Lys Val Pro Met Ala
                645                 650                 655
```

-continued

```
Gly Ser Val Glu Ile Ser Leu Tyr Val Glu Asn Thr Gly Glu Val Glu
            660                 665                 670
Gly Glu Glu Val Val Gln Leu Tyr Ile Gly Arg Glu Cys Ala Ser Val
        675                 680                 685
Thr Arg Pro Val Lys Glu Leu Lys Gly Phe Ala Lys Val Asn Leu Lys
    690                 695                 700
Pro Gly Glu Lys Arg Lys Val Leu Phe Asn Leu His Thr Asp Val Leu
705                 710                 715                 720
Ala Phe Tyr Gly Arg Asp Met Lys Leu Cys Val Glu Pro Gly Val Tyr
                725                 730                 735
Asn Val Met Ile Gly Ser Ser Ser Asp Asp Ile Arg Leu Lys Gly Ser
            740                 745                 750
Phe Glu Val Asp Gly Met Arg Arg Glu Val Phe Glu Asp Arg Val Phe
        755                 760                 765
Phe Thr Lys Val Tyr Thr Phe
770                 775
```